(12) United States Patent
Walker et al.

US010471063B2

(10) Patent No.: US 10,471,063 B2
(45) Date of Patent: *Nov. 12, 2019

(54) DRUG COMBINATION OF PDE3/PDE4 INHIBITOR AND MUSCARINIC RECEPTOR ANTAGONIST

(71) Applicant: VERONA PHARMA PLC, Cardiff (GB)

(72) Inventors: Michael J. A. Walker, Vancouver (CA); Mario Cazzola, Naples (IT); Luigino Calzetta, Rome (IT)

(73) Assignee: Verona Pharma PLC, Cardiff (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/614,440

(22) Filed: Jun. 5, 2017

(65) Prior Publication Data

US 2017/0266190 A1 Sep. 21, 2017

Related U.S. Application Data

(63) Continuation of application No. 14/771,109, filed as application No. PCT/GB2014/050834 on Mar. 17, 2014, now Pat. No. 9,700,558.

(60) Provisional application No. 61/799,177, filed on Mar. 15, 2013.

(51) Int. Cl.
| | | |
|---|---|---|
| A61K 31/519 | (2006.01) | |
| A61K 31/40 | (2006.01) | |
| A61K 45/06 | (2006.01) | |
| A61K 9/00 | (2006.01) | |
| A61K 31/137 | (2006.01) | |
| A61K 31/167 | (2006.01) | |
| A61K 31/44 | (2006.01) | |
| A61K 31/46 | (2006.01) | |
| A61K 9/48 | (2006.01) | |
| A61M 15/00 | (2006.01) | |

(52) U.S. Cl.
CPC ............ *A61K 31/519* (2013.01); *A61K 9/008* (2013.01); *A61K 9/0075* (2013.01); *A61K 9/0078* (2013.01); *A61K 9/0095* (2013.01); *A61K 9/4858* (2013.01); *A61K 31/137* (2013.01); *A61K 31/167* (2013.01); *A61K 31/40* (2013.01); *A61K 31/44* (2013.01); *A61K 31/46* (2013.01); *A61K 45/06* (2013.01); *A61M 15/009* (2013.01); *A61M 2202/064* (2013.01)

(58) Field of Classification Search
None
See application file for complete search history.

(56) References Cited

U.S. PATENT DOCUMENTS

| | | |
|---|---|---|
| 6,794,391 B2 | 9/2004 | Oxford et al. |
| 7,105,663 B2 | 9/2006 | Oxford et al. |
| 7,378,424 B2 | 5/2008 | Oxford et al. |
| 8,242,127 B2 | 8/2012 | Oxford et al. |
| 9,062,047 B2 | 6/2015 | Walker et al. |
| 2003/0036542 A1 | 2/2003 | Oxford et al. |
| 2004/0171828 A1 | 9/2004 | Oxford et al. |
| 2004/0176353 A1 | 9/2004 | Oxford et al. |
| 2005/0267135 A1 | 12/2005 | Escardo |
| 2008/0206163 A1 | 8/2008 | Oxford et al. |
| 2009/0136429 A1* | 5/2009 | Maus ................... A61K 9/0073 424/43 |
| 2010/0009934 A1 | 1/2010 | Rickles et al. |
| 2012/0302533 A1 | 11/2012 | Oxford et al. |
| 2013/0225616 A1 | 8/2013 | Walker et al. |
| 2016/0008363 A1 | 1/2016 | Walker et al. |

FOREIGN PATENT DOCUMENTS

| | | |
|---|---|---|
| CA | 2439763 A1 | 9/2002 |
| EP | 2 111 861 A1 | 10/2009 |
| JP | 2004-521134 A | 7/2004 |
| JP | 2008-545651 A | 12/2008 |
| JP | 2012-184272 A | 9/2012 |
| JP | 2012-211183 A | 11/2012 |
| WO | 98/00119 A | 1/1998 |
| WO | 2000/058308 A1 | 10/2000 |
| WO | 2005/115462 A1 | 12/2005 |
| WO | 2005/115465 A1 | 12/2005 |
| WO | 2006/124676 A1 | 11/2006 |
| WO | 2007/045980 A1 | 4/2007 |
| WO | 2012/020016 A1 | 2/2012 |

OTHER PUBLICATIONS

Tanaka, Chikako and Ryuichi Kato, editors, New Pharmacology, Nov. 20, 2012, Revised 6th Edition, 3rd Print, pp. 480-481.
Yanagisawa, Teruyuki, author and editor, Introduction to New Pharmacology, Nanzando, Mar. 12, 2003, 2nd Edition, 1st Print, pp. 96.
Office Action in corresponding Japanese Patent Application No. 562338/2015, dated Jan. 9, 2018, 12 pages. (Japanese and English).
International Search Report corresponding to PCT/GB2014/050834 dated May 6, 2014; 7 pages.
ATS Journals "RPL554, A dual Phosphodiesterase (PDE) 3/4 Inhibitor Acts Synergistically with Muscarinic Receptor Antagonists and Beta-Adrenoceptor Agonists to Produce Bronchodilator In Vivo," *American Journal of Respiratory and Critical Care Medicine Home* (online May 1, 2014 as doi:10.1164/ajrccm-conference.2014.189. 1_Meeting Abstracts.A4218; 3 pages.

(Continued)

*Primary Examiner* — Bong-Sook Baek
(74) *Attorney, Agent, or Firm* — Kilpatrick Townsend & Stockton LLP

(57) ABSTRACT

The invention provides a composition which comprises (a) a PDE3/PDE4 inhibitor which is 9,10-Dimethoxy-2-(2,4,6-trimethylphenylimino)-3-(N-carbamoyl-2-aminoethyl)-3,4, 6,7-tetrahydro-2H-pyrimido[6,1-a]isoquinolin-4-one or a pharmaceutically acceptable acid addition salt thereof and (b) a muscarinic receptor antagonist.

10 Claims, 11 Drawing Sheets

(56) References Cited

OTHER PUBLICATIONS

Boswell-Smith et al., "The Pharmacology of Two Novel Long-Acting Phosphodiesterase ¾ Inhibitors, RPL554 [9,10-Dimethoxy-2(2,4,6-trimethylphenylimino)-3-(N-carbamoyl-2-aminoethyl)-3,4,6,7-tetrahydro-2H-pyrimido[6,1-a]isoquinolin-4-one] and RPL565 [6,7-Dihydro-2-(2,6-diisopropylphenoxy)-9,10-dimethoxy-4H-pyrimido[6,1-a]isoquinolin-4-one]," *The Journal of Pharmacology and Experimental Therapeutics* (May 4, 2006); 318(2):840-848.

Calzetta, Luigino et al., "Effect of the Mixed Phosphodiesterase 3/4 Inhibitor RPL554 on Human Isolated Bronchial Smooth Muscle Tone," *The Journal of Pharmacology and Experimental Therapeutics* (Sep. 1, 2013); 346:414-423.

Calzetta, Luigino, A Thesis under the title, "Factors Influencing the Responsiveness of Human Bronchi," King's College London, University of London, Oct. 2012, p. 192-205, 16 pages.

Franciosi L. et al., "RPL554, A Dual Pde3/4 Inihibitor, Is Well Tolerated and Maintains Bronchodilator Activity When Administered by Inhalation to Mild-To-Moderate Allergic Asthmatics on 6 Consecutive Days," *Am. J. Respir. Crit. Care Med.* (May 21, 2013); online Abstracts; 1 page.

Franciosi, Lui G. et al., "Efficacy and safety of RPL554, a dual PDE3 and PDE4 inhibitor, in healthy volunteers and in patients with asthma or chronic obstructive pulmonary disease: findgs from four clinical trials," *The Lancet Respiratory Medicine* (published online Oct. 25, 2013); 14 pages.

Harvey et al, Lippincott's Illustrated Reviews: Pharmacology, 2nd ed., Lippincott Williams & Wilkins, 2000, p. 217-218, 4 pages.

Parkkonen, Jouni et al., "Phosphodiesterase 4 inhibitors delay human eosinophil and neutrophil apoptosis in the absence and presence of salbutamol," *Pulmonary Pharmacology & Therapeutics* (Jun. 1, 2008); 21(3):499-506.

Office Action dated Oct. 30, 2018 in counterpart Japanese Patent Application No. 562338/2015; in Japanese with English translation; 16 pages.

\* cited by examiner

DRUG COMBINATION OF PDE3/PDE4 INHIBITOR AND MUSCARINIC RECEPTOR ANTAGONIST

CROSS-REFERENCE TO RELATED APPLICATIONS

This application is a continuation of U.S. patent application Ser. No. 14/771,109 filed Oct. 29, 2015 (now U.S. Pat. No. 9,700,558), which is a national stage application under 35 U.S.C. 371 of International Patent Application No. PCT/GB2014/050834 filed Mar. 17, 2014, which claims the benefit of U.S. Provisional Patent Application No. 61/799,177 filed Mar. 15, 2013, the teachings of which are hereby incorporated by reference in their entireties for all purposes.

This application claims priority from U.S. provisional patent application No. 61/799,177 filed 15 Mar. 2013, which is incorporated by reference.

FIELD OF THE INVENTION

The present invention relates to a new combination of drugs which has surprising therapeutic efficacy in the treatment of respiratory and inflammatory disorders.

BACKGROUND OF THE INVENTION

There are a number of different therapeutic approaches to treating respiratory diseases such as asthma and chronic obstructive pulmonary disease (COPD). For example, corticosteroids, $\beta_2$-adrenergic receptor agonists, phosphodiesterase (PDE) 4 inhibitors, PDE 3 inhibitors, leukotriene receptor antagonists, epidermal growth factor receptor (egfr) kinase inhibitors, p38 kinase inhibitors, NK1 agonists and muscarinic receptor antagonists are all known for use in the treatment of respiratory diseases.

RPL554 (9,10-Dimethoxy-2-(2,4,6-trimethylphenylimino)-3-(N-carbamoyl-2-aminoethyl)-3,4,6,7-tetrahydro-2H-pyrimido[6,1-a]isoquinolin-4-one) is a dual PDE3/PDE4 inhibitor and is described in WO 00/58308. As a combined PDE3/PDE4 inhibitor, RPL554 has both anti-inflammatory and bronchodilatory activity and is useful in the treatment of respiratory disorders such as asthma and chronic obstructive pulmonary disease (COPD).

It is known that different classes of respiratory drugs may be used in combination for the treatment of respiratory diseases. However, synergistic interaction between the components of such combinations is rarely observed.

SUMMARY OF THE INVENTION

It is a surprising finding of the present invention that RPL554 is capable of potentiating the activity of muscarinic receptor antagonists. RPL554 and muscarinic receptor antagonists therefore interact synergistically in combination to provide an improved therapeutic effect.

True synergistic interactions between drugs are rare. The presence of a synergistic interaction can be determined by, for example, the Berenbaum method, the Bliss Independence (BI) criterion and/or the Loewe Additivity (LA) model through curved isoboles (see Berenbaum, 1977; Greco et al., 1995; Grabovsky and Tallarida, 2004; Tallarida, 2006; Goldoni and Johansson, 2007; Tallarida and Raffa, 2010).

According to the Berenbaum method, synergy for a combination is detected by first determining dose-response curves for each of the constituent drugs as monotherapies in order to identify a low and high dose of each drug. The effect of a combination of the low doses of each drug is then measured. If a combination of the low doses of each drug produces a greater response than either high dose alone as monotherapy, then there is true synergy between the two drugs.

The present inventors have surprisingly found that a true synergistic effect according to the Berenbaum method arises when RPL554 is combined with a muscarinic receptor antagonist.

The enhanced therapeutic effect that is obtained whilst using low doses of each constituent drug is highly desirable in a clinical context, and for example reduces the side effects experienced by the patient.

Accordingly, the present invention provides a composition which comprises (a) a PDE3/PDE4 inhibitor which is 9,10-Dimethoxy-2-(2,4,6-trimethylphenylimino)-3-(N-carbamoyl-2-aminoethyl)-3,4,6,7-tetrahydro-2H-pyrimido[6,1-a]isoquinolin-4-one or a pharmaceutically acceptable acid addition salt thereof and (b) a muscarinic receptor antagonist.

The invention also provides a pharmaceutical composition comprising a composition according to the invention and one or more pharmaceutically acceptable carriers, diluents, or excipients The invention also provides a method of treating a disease or condition which is based on (i) acute or chronic obstruction of vessels or bronchi or (ii) acute or chronic inflammation, in a subject in need thereof, which method comprises administering to said subject (a) a PDE3/PDE4 inhibitor as defined herein and (b) a muscarinic receptor antagonist.

The invention also provides a product comprising (a) a PDE3/PDE4 inhibitor as defined herein and (b) a muscarinic receptor antagonist for simultaneous, separate or sequential use in the treatment of a disease or condition as defined herein.

The invention also provides use of (a) a PDE3/PDE4 inhibitor as defined herein in the manufacture of a medicament for simultaneous, separate or sequential use in the treatment of a disease or condition as defined herein in combination with (b) a muscarinic receptor antagonist.

The invention also provides use of (b) a muscarinic receptor antagonist in the manufacture of a medicament for simultaneous, separate or sequential use in the treatment of a disease or condition as defined herein in combination with (a) a PDE3/PDE4 inhibitor as defined herein.

The invention also provides use of (a) a PDE3/PDE4 inhibitor as defined herein and (b) a muscarinic receptor antagonist in the manufacture of a medicament for use in the treatment of a disease or condition as defined herein.

The invention also provides a composition of the invention for use in the treatment of a disease or condition as defined herein.

The invention also provides a PDE3/PDE4 inhibitor as defined herein for use in the treatment of a disease or condition as defined herein in combination with a muscarinic receptor antagonist.

The invention also provides a muscarinic receptor antagonist for use in the treatment of a disease or condition as defined herein in combination with a PDE3/PDE4 inhibitor as defined herein.

DETAILED DESCRIPTION OF THE INVENTION

Figure 1:
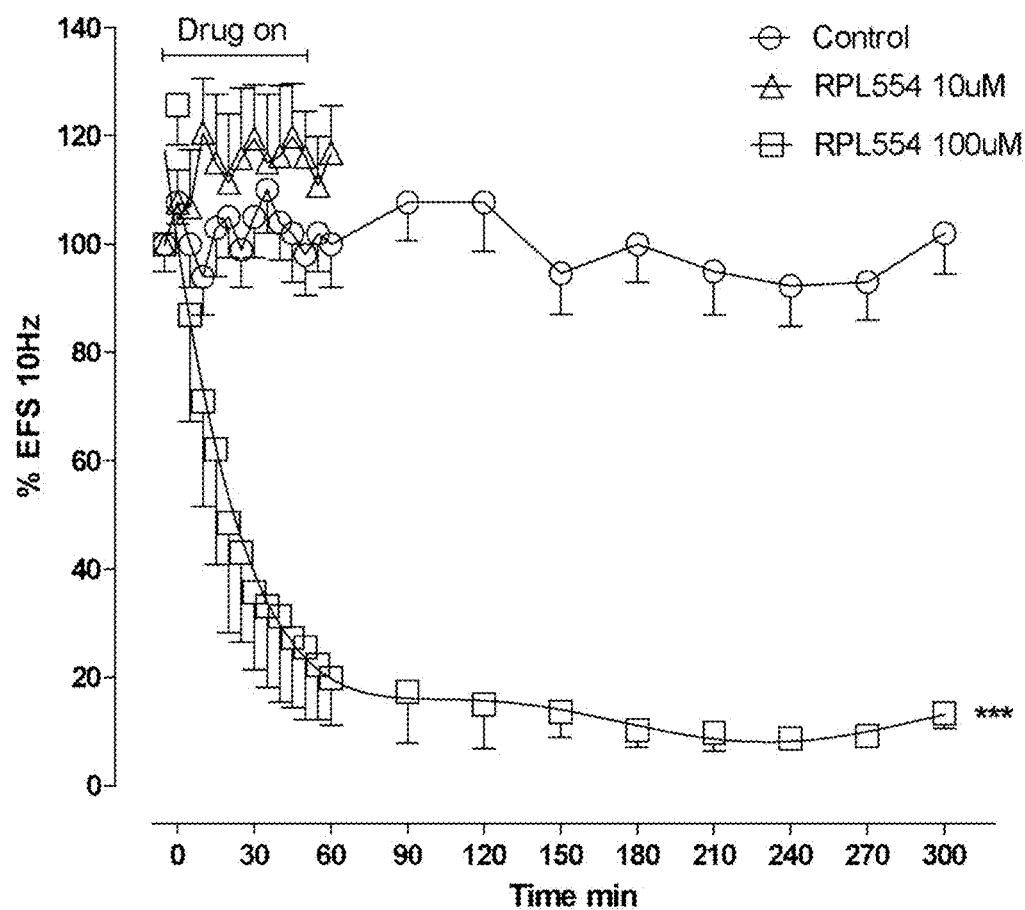
FIG. 1: Line graph representing inhibition of contraction of human isolated bronchial preparations to EFS following 50 min incubation with RPL554. Points shown are from experiments performed with samples of n=5 different subjects and they are represented as mean±SEM; ***P<0.001 vs control.

The following abbreviations are used herein:
RPL554: 9,10-Dimethoxy-2-(2,4,6-trimethylphenylimino)-3-(N-carbamoyl-2-aminoethyl)-3,4,6,7-tetrahydro-2H-pyrimido[6,1-a]isoquinolin-4-one; ANOVA: analysis of variance; BI: Bliss Independence; COX: cyclooxygenase; EC30: concentration required to cause a 30% maximal effect; EC50: concentration required to cause a 50% maximal effect; EC70: concentration required to cause a 70% maximal effect; EFS: electrical field stimulation; Emax: maximal effect; KH: Krebs-Henseleit buffer solution; LA: Loewe Additivity; and PDE: phosphodiesterase.

The term "pharmaceutically acceptable" refers to a material that is not biologically or otherwise undesirable. For example, the term "pharmaceutically acceptable carrier" refers to a material that can be incorporated into a composition and administered to a subject/patient without causing undesirable biological effects or interacting in a deleterious manner with other components of the composition. Such pharmaceutically acceptable materials typically have met the required standards of toxicological and manufacturing testing, and include those materials identified as suitable inactive ingredients by the U.S. Food and Drug administration.

The term "pharmaceutically acceptable acid addition salt" refers to an acid addition salt of a pharmaceutical which is not biologically or otherwise undesirable. Such pharmaceutically acceptable acid addition salts are well known to the skilled person.

The term "therapeutically effective amount" means an amount sufficient to effect treatment when administered to a subject in need of treatment. In particular, an "effective" amount is that amount needed to obtain the desired result, and a "therapeutically effective" amount is that amount needed to obtain the desired therapeutic effect. For example, for antagonizing a muscarinic receptor, an "effective amount" is a muscarinic-receptor-antagonizing amount. Similarly, a therapeutically effective amount for treating chronic obstructive pulmonary disease (COPD) is that amount that will achieve the desired therapeutic result, which may be disease prevention, amelioration, suppression or alleviation.

The term "treating" or "treatment" as used herein means the treating or treatment of a disease or medical condition (such as COPD) in a subject, such as a mammal (particularly a human) that includes: (a) preventing the disease or medical condition from occurring, i.e., prophylactic treatment of a subject; (b) ameliorating the disease or medical condition, i.e., eliminating or causing regression of the disease or medical condition in a subject; (c) suppressing the disease or medical condition, i.e., slowing or arresting the development of the disease or medical condition in a subject; or (d) alleviating the symptoms of the disease or medical condition in a subject. For example, the term "treating COPD" would include preventing COPD from occurring, ameliorating COPD, suppressing COPD, and alleviating the symptoms of COPD. The term "subject" is intended to include those animals, such as humans, that are in need of treatment or disease prevention, that are presently being treated for disease prevention or treatment of a specific disease or medical condition, as well as test subjects in which compositions of the invention are being evaluated or being used in an assay, for example an animal model.

The PDE3/PDE4 Inhibitor

The PDE3/PDE4 inhibitor used in the present invention is 9,10-Dimethoxy-2-(2,4,6-trimethylphenylimino)-3-(N-carbamoyl-2-aminoethyl)-3,4,6,7-tetrahydro-2H-pyrimido[6,1-a]isoquinolin-4-one (also known as RPL554) or a pharmaceutically acceptable acid addition salt thereof.

Typically, the PDE3/PDE4 inhibitor is 9,10-Dimethoxy-2-(2,4,6-trimethylphenylimino)-3-(N-carbamoyl-2-aminoethyl)-3,4,6,7-tetrahydro-2H-pyrimido[6,1-a]isoquinolin-4-one. Thus the free base of 9,10-Dimethoxy-2-(2,4,6-trimethylphenylimino)-3-(N-carbamoyl-2-aminoethyl)-3,4,6,7-tetrahydro-2H-pyrimido[6,1-a]isoquinolin-4-one is preferred.

Muscarinic Receptor Antagonists

A muscarinic receptor antagonist (MRA) is a compound that blocks the activity of muscarinic acetylcholine receptors. A skilled person can determine whether a given compound blocks the activity of muscarinic acetylcholine receptors without difficulty using assays well known to those skilled in the art.

It is a finding of the present invention that RPL554 is capable of potentiating the activity of two structurally distinct muscarinic receptor antagonists, namely atropine and glycopyrronium. Based on this finding with two structurally distinct muscarinic receptor antagonists, it follows that synergistic interaction observed with RPL554 arises due to the activity of those compounds as muscarinic receptor antagonists, rather than due to the specific structure of those compounds. It therefore follows that a synergistic interaction with RPL554 can be expected with all compounds with muscarinic receptor antagonist activity.

Typically, the muscarinic receptor antagonist is atropine, methylatropine, homatropine, hyoscyamine, scopolamine, ipratropium, oxitropium, tiotropium, methantheline, propantheline, anisotropine, clidinium, copyrrolate (Robinul), isopropamide, mepenzolate, tridihexethyl, hexocyclium, cyclopentolate, tropicamide, trihexyphenidyl, pirenzepine, telenzepine, AF-DX 116 and methoctramine or the like. For example, the muscarinic receptor antagonist is atropine, atropine sulfate, atropine oxide, methylatropine nitrate, homatropine hydrobromide, hyoscyamine (d, 1) hydrobromide, scopolamine hydrobromide, ipratropium bromide, oxitropium bromide, tiotropium bromide, methantheline, propantheline bromide, anisotropine methyl bromide, clidinium bromide, copyrrolate (Robinul), isopropamide iodide, mepenzolate bromide, tridihexethyl chloride (Pathilone), hexocyclium methylsulfate, cyclopentolate hydrochloride, tropicamide, trihexyphenidyl hydrochloride, pirenzepine, telenzepine, AF-DX 116 and methoctramine or the like. Other representative examples of muscarinic receptor antagonists include aclidinium (for instance aclidinium bromide) and umeclidinium (for instance umeclidinium bromide).

Typically, the muscarinic receptor antagonist is atropine, hyoscine, glycopyrrolate (glycopyrronium), ipratropium, tiotropium, oxitropium, pirenzepine, telenzepine, aclidinium or umeclidinium. Preferably, the muscarinic receptor antagonist may be atropine, hyoscine, glycopyrrolate (glycopyrronium), ipratropium bromide, tiotropium bromide, oxitropium bromide, pirenzepine, telenzepine, aclidinium or umeclidinium. Alternatively, the muscarinic receptor antagonist may be atropine, hyoscine, glycopyrrolate, ipratropium bromide, tiotropium bromide, oxitropium bromide, pirenzepine, or telenzepine.

More preferably, the muscarinic receptor antagonist is atropine, ipratropium bromide or tiotropium bromide.

Most preferably, the muscarinic receptor agonist is atropine or glycopyrronium.

The muscarinic receptor antagonists are optionally in the form of their racemates, their enantiomers, their diastereomers, and mixtures thereof, and optionally their pharmaceutically acceptable acid addition salts. Typical examples of suitable acids for the formation of addition salts of the muscarinic receptor antagonists are hydrochloric acid, hydrobromic acid, sulphuric acid, phosphoric acid, methanosulphonic acid, acetic acid, fumaric acid, succinic acid, maleic acid, and trifluoroacetic acid. Furthermore, mixtures of the aforementioned salts can be used.

Compositions, Combinations, Pharmaceutical Compositions and Formulations

The compositions of the invention comprise (a) a PDE3/PDE4 inhibitor which is 9,10-Dimethoxy-2-(2,4,6-trimethylphenylimino)-3-(N-carbamoyl-2-aminoethyl)-3,4,6,7-tetrahydro-2H-pyrimido[6,1-a]isoquinolin-4-one or a pharmaceutically acceptable acid addition salt thereof and (b) a muscarinic receptor antagonist.

Typically, the composition of the invention is a fixed combination. In a fixed combination, the PDE3/PDE4 inhibitor and the muscarinic receptor antagonist are present in the same composition. The fixed combination can be used for simultaneous administration of the PDE3/PDE4 inhibitor and the muscarinic receptor antagonist. Typically, the fixed combination is a dry powder composition (which is preferably suitable for delivery from a dry powder inhaler), a solution which is suitable for delivery from a nebulizer, or a solution or suspension which is suitable for delivery from a pressurised metered dose inhaler.

Thus, for example, the fixed combination is preferably a dry powder composition comprising both the PDE3/PDE4 inhibitor and the muscarinic receptor antagonist. Alternatively, the fixed combination can be a solution, typically an aqueous solution, comprising both the PDE3/PDE4 inhibitor and the muscarinic receptor antagonist, which is suitable for delivery from a nebulizer. Alternatively, the fixed combination can be a solution or suspension comprising both the PDE3/PDE4 inhibitor and the muscarinic receptor antagonist, which is suitable for delivery from a pressurised metered dose inhaler.

The two components in a fixed combination are typically intermixed.

Alternatively, the composition of the invention may be a free combination. In a free combination, the active components (a) and (b) are typically separate from each other and packaged in one unit for simultaneous, substantially simultaneous, separate or sequential administration.

Typically, the composition is a pharmaceutical composition which further comprises one or more pharmaceutically acceptable carriers, diluents, or excipients in addition to the PDE3/PDE4 inhibitor and the muscarinic receptor antagonist. The compositions may contain other therapeutic and/or formulating agents if desired. A preferred example of another therapeutic agent is a $\beta_2$-adrenergic receptor agonist. Examples of $\beta_2$-adrenergic receptor agonists are salbutamol, albuterol, bitolterol, fenoterol, formoterol, indacaterol, isoetharine, levalbuterol, metaproterenol, pirbuterol, salmefamol, salmeterol and terbutaline. Preferred examples of $\beta_2$-adrenergic receptor agonists are salbutamol, salmeterol, formoterol, albuterol and pirbuterol.

Compositions of the present invention are typically administered to a subject in the form of a pharmaceutical composition. Such pharmaceutical compositions may be administered to the subject by any acceptable route of administration including, but not limited to, inhaled, oral, nasal, topical (including transdermal) and parenteral modes of administration. Administration by inhalation is preferred. Further, the compositions of the invention may be administered, for example orally, in multiple doses per day, in a single daily dose or a single weekly dose. It will be understood that any form of the active agents used in the composition of the invention, (i.e. free base, pharmaceutically acceptable salt, solvate, etc.) that is suitable for the particular mode of administration can be used in the pharmaceutical compositions discussed herein.

The pharmaceutical compositions of this invention typically contain a therapeutically effective amount of an active agent. Those skilled in the art will recognize, however, that a pharmaceutical composition may contain more than a therapeutically effective amount, i.e., bulk compositions, or less than a therapeutically effective amount, i.e., individual unit doses designed for multiple administration to achieve a therapeutically effective amount. In one embodiment, the composition will contain from about 0.01-95 wt % of active agent, including, from about 0.01-30 wt %, such as from about 0.01-10 wt %, with the actual amount depending upon the formulation itself, the route of administration, the frequency of dosing, and so forth. In another embodiment, a composition suitable for inhalation, for example, comprises from about 0.01-30 wt % or active agent with yet another embodiment comprises from about 0.01-10 wt % active agent.

Any conventional carrier or excipient may be used in the pharmaceutical compositions of the invention. The choice of a particular carrier or excipient, or combinations of carriers or excipients, will depend on the mode of administration being used to treat a particular subject or type of medical condition or disease state. In this regard, the preparation of a suitable composition for a particular mode of administration is well within the scope of those skilled in the pharmaceutical arts. Additionally, carriers or excipients used in such compositions are commercially available. By way of further illustration, conventional formulation techniques are described in Remington: The Science and Practice of Pharmacy, 20$^{th}$ Edition, Lippincott Williams & White, Baltimore, Md. (2000); and H. C. Ansel et al., Pharmaceutical Dosage Forms and Drug Delivery Systems, 7$^{th}$ Edition, Lippincott Williams & White, Baltimore, Md. (1999).

Representative examples of materials which can serve as pharmaceutically acceptable carriers include, but are not limited to, the following: sugars, such as lactose, glucose and sucrose; starches, such as corn starch and potato starch; cellulose, such as microcrystalline cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; compressed propellant gases, such as chlorofluorocarbons and hydrofluorocarbons; and other non-toxic compatible substances employed in pharmaceutical compositions. Pharmaceutical compositions are typically prepared by thoroughly and intimately mixing or blending the active agent/active ingredient with a pharmaceutically acceptable carrier and one or more optional ingredients. The resulting uniformly blended mixture may then be shaped or loaded into tablets, capsules, pills, canisters, cartridges, dispensers and the like using conventional procedures and equipment.

Typically, the pharmaceutical compositions are suitable for inhaled administration. The pharmaceutical composition may be for administration by dry powder inhaler (DPI) or metered-dose inhaler (MDI).

Suitable compositions for inhaled administration will typically be in the form of an aerosol or a powder, for instance a dry powder composition. Such compositions are generally administered using well-known delivery devices, such as a nebulizer inhaler, a dry powder inhaler, or a metered-dose inhaler, examples of which are described below.

Alternatively, a composition comprising the active agent(s)/active ingredient(s) may be administered by inhalation using a nebulizer inhaler. Such nebulizer devices typically produce a stream of high velocity air that causes the composition to spray as a mist that is carried into a subject's respiratory tract. Accordingly, when formulated for use in a nebulizer inhaler, the active agent(s)/active ingredient(s) is typically dissolved in a suitable carrier to form a solution. Alternatively, the active agent(s)/active ingredient(s) can be micronized and combined with a suitable carrier to form a suspension of micronized particles of respirable size, where micronized is typically defined as having particles in which at least about 90 percent of the particles have a mass median diameter of less than about 10 μm. The term "mass median diameter" means the diameter such that half the mass of the particles is contained in particles with larger diameter and half is contained in particles with smaller diameter.

Suitable nebulizer devices include the Respimat® Soft Mist™ Inhaler (Boehringer Ingelheim), the AERx® Pulmonary Delivery System (Aradigm Corp.), and the PARI LC Plus Reusable Nebulizer (Pari GmbH). An exemplary composition for use in a nebulizer inhaler comprises an isotonic aqueous solution comprising from about 0.05 μg/mL to about 10 mg/mL of a RPL554. In one embodiment, such a solution has a pH of about 3.5-6.

Alternatively, a composition comprising the active agent(s)/active ingredient(s) may be administered by inhalation using a dry powder inhaler (DPI). Such DPIs typically administer the active agent as a free-flowing powder that is dispersed in a subject's air-stream during inspiration. In order to achieve a free flowing powder, the active agent(s)/active ingredient(s) is typically formulated with a suitable excipient such as lactose, starch, mannitol, dextrose, polylactic acid, polylactide-co-glycolide, and combinations thereof. Typically, the active agent(s)/active ingredient(s) is micronized and combined with an excipient to form a blend suitable for inhalation. Accordingly, in one embodiment of the invention, the active agent(s)/active ingredient(s) is in micronized form. For example, a representative composition for use in a DPI comprises dry lactose having a particle size between about 1 μm and about 100 μm (e.g., dry milled lactose) and micronized particles of the active agent. Such a dry powder formulation can be made, for example, by combining lactose with the active agent and then dry blending the components. Alternatively, if desired, the active agent can be formulated without an excipient. The composition is then typically loaded into a DPI, or into inhalation cartridges or capsules for use with a DPI. DPIs are well known to those of ordinary skill in the art, and many such devices are commercially available, with representative devices including Aerolizer® (Novartis), Airmax® (IVAX), ClickHaler® (Innovata Biomed), Diskhaler® (GlaxoSmithKline), Diskus® or Accuhaler (GlaxoSmithKline), Easyhaler® (Orion Pharma), Eclipse™ (Aventis), FlowCaps® (Hovione), Handihaler® (Boehringer Ingelheim), Pulvinal® (Chiesi), Rotahaler® (GlaxoSmithKline), SkyeHaler™ or Certihaler™ (SkyePharma), Twisthaler (Schering-Plough), Turbuhaler® (AstraZeneca), Ultrahaler® (Aventis), and the like. Alternatively, the composition comprising the active agent may be administered by inhalation using a metered-dose inhaler (MDI). Such MDIs typically discharge a measured amount of the active agent using compressed propellant gas. Metered-dose formulations thus typically comprise a solution or suspension of the active agent in a liquefied propellant, such as a chlorofluorocarbon such as $CCl_3F$ or a hydrofluoroalkane (HFA) such as 1,1,1,2-tetrafluoroethane (HFA 134a) and 1,1,1,2,3,3,3-heptafluoro-n-propane (HFA 227), although HFAs are generally preferred due to concerns about chlorofluorocarbons affecting the ozone layer. Additional optional components of HFA formulations include co-solvents, such as ethanol or pentane, and surfactants, such as sorbitan trioleate, oleic acid, lecithin, and glycerin. See, for example, U.S. Pat. No. 5,225,183 to Purewal et al., EP 0717987 A2 (Minnesota Mining and Manufacturing Company), and WO 92/22286 (Minnesota Mining and Manufacturing Company). A representative composition for use in an MDI comprises from about 0.01-5 wt % of active agent; from about 0-20 wt % ethanol; and from about 0-5 wt % surfactant; with the remainder being an HFA propellant. Such compositions are typically prepared by adding a chilled or pressurized hydrofluoroalkane to a suitable container containing the active agent, ethanol (if present) and the surfactant (if present). To prepare a suspension, the active agent is micronized and then combined with the propellant. The formulation is then loaded into an aerosol canister, which forms a portion of the MDI. MDIs are well known to those of ordinary skill in the art, and many such devices are commercially available, with representative devices including AeroBid Inhaler System (Forest Pharmaceuticals), Atrovent Inhalation Aerosol (Boehringer Ingelheim), Flovent® (GlaxoSmithKline), Maxair Inhaler (3M), Proventil® Inhaler (Schering), Serevent® Inhalation Aerosol (GlaxoSmithKline), and the like. Alternatively, a suspension formulation can be prepared by spray drying a coating of surfactant on micronized particles of the active agent. See, for example, WO 99/53901 (Glaxo Group Ltd.) and WO 00/61108 (Glaxo Group Ltd.).

Additional examples of processes of preparing respirable particles, and formulations and devices suitable for inhalation dosing are described in U.S. Pat. No. 5,874,063 to Briggner et al.; U.S. Pat. No. 5,983,956 to Trofast; U.S. Pat. No. 6,221,398 to Jakupovic et al.; U.S. Pat. No. 6,268,533 to Gao et al.; U.S. Pat. No. 6,475,524 to Bisrat et al.; and U.S. Pat. No. 6,613,307 to Cooper.

Alternatively, the pharmaceutical compositions may be suitable for oral administration. Suitable compositions for oral administration may be in the form of capsules, tablets, pills, lozenges, cachets, dragees, powders, granules; solutions or suspensions in an aqueous or non-aqueous liquid; oil-in-water or water-in-oil liquid emulsions; elixirs or syrups; and the like; each containing a predetermined amount of the active agent.

When intended for oral administration in a solid dosage form (i.e., as capsules, tablets, pills and the like), the composition will typically comprise the active agent and one or more pharmaceutically acceptable carriers, such as sodium citrate or dicalcium phosphate. Solid dosage forms may also comprise: fillers or extenders, such as starches, microcrystalline cellulose, lactose, sucrose, glucose, mannitol, and/or silicic acid; binders, such as carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and/or sodium carbonate; solution retarding agents, such as paraffin; absorption accelerators, such as quaternary ammonium compounds; wetting agents, such as cetyl alcohol and/or glycerol monostearate; absorbents, such as kaolin and/or bentonite clay; lubricants, such as talc, calcium stearate, magnesium stearate, solid polyethylene glycols, sodium lauryl sulfate, and/or mixtures thereof; coloring agents; and buffering agents.

Release agents, wetting agents, coating agents, sweetening, flavoring and perfuming agents, preservatives and antioxidants may also be present in the pharmaceutical compositions. Exemplary coating agents for tablets, capsules, pills and like, include those used for enteric coatings, such as cellulose acetate phthalate, polyvinyl acetate phthalate, hydroxypropyl methylcellulose phthalate, methacrylic acid-methacrylic acid ester copolymers, cellulose acetate trimellitate, carboxymethyl ethyl cellulose, hydroxypropyl methyl cellulose acetate succinate, and the like. Examples of pharmaceutically acceptable antioxidants include: water-soluble antioxidants, such as ascorbic acid, cysteine hydrochloride, sodium bisulfate, sodium metabisulfate sodium sulfite and the like; oil-soluble antioxidants, such as ascorbyl palmitate, butylated hydroxyanisole, butylated hydroxytoluene, lecithin, propyl gallate, alpha-tocopherol, and the like; and metal-chelating agents, such as citric acid, ethylenediamine tetraacetic acid, sorbitol, tartaric acid, phosphoric acid, and the like.

Compositions may also be formulated to provide slow or controlled release of the active agent using, by way of example, hydroxypropyl methyl cellulose in varying proportions or other polymer matrices, liposomes and/or microspheres. In addition, the pharmaceutical compositions of the invention may contain opacifying agents and may be formulated so that they release the active agent only, or preferentially, in a certain portion of the gastrointestinal tract, optionally, in a delayed manner. Examples of embedding compositions which can be used include polymeric substances and waxes. The active agent can also be in micro-encapsulated form, if appropriate, with one or more of the above-described excipients. Suitable liquid dosage forms for oral administration include, by way of illustration, pharmaceutically acceptable emulsions, microemulsions, solutions, suspensions, syrups and elixirs. Liquid dosage forms typically comprise the active agent and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (e.g., cottonseed, groundnut, corn, germ, olive, castor and sesame oils), glycerol, tetrahydrofuryl alcohol, polyethylene glycols and fatty acid esters of sorbitan, and mixtures thereof. Suspensions may contain suspending agents such as, for example, ethoxylated isostearyl alcohols, polyoxyethylene sorbitol and sorbitan esters, microcrystalline cellulose, aluminium metahydroxide, bentonite, agar-agar and tragacanth, and mixtures thereof.

When intended for oral administration, the pharmaceutical compositions of the invention may be packaged in a unit dosage form. The term "unit dosage form" refers to a physically discrete unit suitable for dosing a subject, i.e., each unit containing a predetermined quantity of the active agents calculated to produce the desired therapeutic effect either alone or in combination with one or more additional units. For example, such unit dosage forms may be capsules, tablets, pills, and the like.

Compositions of the invention can also be administered parenterally (e.g., by subcutaneous, intravenous, intramuscular, or intraperitoneal injection). For such administration, the active agents are provided in a sterile solution, suspension, or emulsion. Exemplary solvents for preparing such formulations include water, saline, low molecular weight alcohols such as propylene glycol, polyethylene glycol, oils, gelatin, fatty acid esters such as ethyl oleate, and the like. A typical parenteral formulation is a sterile pH 4-7 aqueous solution of the active agents. Parenteral formulations may also contain one or more solubilizers, stabilizers, preservatives, wetting agents, emulsifiers, and dispersing agents. These formulations may be rendered sterile by use of a sterile injectable medium, a sterilizing agent, filtration, irradiation, or heat.

Compositions of the invention can also be administered transdermally using known transdermal delivery systems and excipients. For example, the active agents can be admixed with permeation enhancers, such as propylene glycol, polyethylene glycol monolaurate, azacycloalkan-2-ones and the like, and incorporated into a patch or similar delivery system. Additional excipients including gelling agents, emulsifiers and buffers, may be used in such transdermal compositions if desired.

By combining RPL554 with a secondary agent, double therapy can be achieved, i.e., PDE3/PDE4 inhibition activity and activity associated with the secondary agent (muscarinic receptor antagonist), in some cases by administering two compositions and in some cases by administering a single composition containing the active agent and the secondary agent. In combination therapy, the amount of RPL554 that is administered, as well as the amount of secondary agents, may be less than the amount typically administered in monotherapy.

RPL554 may be either physically mixed with the second active agent (muscarinic receptor antagonist) to form a composition containing both agents; or each agent may be present in separate and distinct compositions which are administered to the subject simultaneously or sequentially. For example, RPL554 can be combined with a second active agent using conventional procedures and equipment to form a combination of active agents comprising RPL554 and a second active agent. Additionally, the active agents may be combined with a pharmaceutically acceptable carrier to form a pharmaceutical composition comprising RPL554, a second active agent and a pharmaceutically acceptable carrier. In this embodiment, the components of the composition are typically mixed or blended to create a physical mixture. The physical mixture is then administered in a therapeutically effective amount using any of the routes described herein.

Alternatively, the active agents may remain separate and distinct before administration to the subject. In this embodiment, the agents are not physically mixed together before administration but are administered simultaneously or at separate times as separate compositions. Such compositions can be packaged separately or may be packaged together in a kit. When administered at separate times, the secondary agent will typically be administered less than 24 hours after administration of RPL554. In other embodiments this timed relationship is less than 12 hours, less than 8 hours, less than 6 hours, less than 4 hours, less than 3 hours, less than 1 hour, less than thirty minutes, less than ten minutes, less than one minute, or immediately after administration of RPL554. This is also referred to as sequential administration. Thus, RPL554 can be administered by inhalation simultaneously or sequentially with another active agent using an inhalation delivery device that employs separate compartments (e.g. blister packs) for each active agent, where sequential may mean being administered immediately after administration of RPL554 or at some predetermined time later (e.g., one hour later or three hours later). Alternatively, the combination may be administered using separate delivery devices, i.e., one delivery device for each agent. Additionally, the agents can be delivered by different routes of administration, i.e., one by inhalation and the other by oral administration.

Typically, the kit comprises a first dosage form comprising RPL554 and at least one additional dosage form comprising one or more of the secondary agents set forth herein, in quantities sufficient to carry out the methods of the invention. The first dosage form and the second (or third, etc,) dosage form together comprise a therapeutically effective amount of active agents for the treatment or prevention of a disease or medical condition in a subject. Secondary agent(s), when included, are present in a therapeutically effective amount. i.e., are typically administered in an amount that produces a therapeutically beneficial effect when co-administered with RPL554. The secondary agent can be in the form of a pharmaceutically acceptable acid addition salt, solvate, optically pure stereoisomer, and so forth. Thus, secondary agents listed below are intended to include all such forms, and are commercially available or can be prepared using conventional procedures and reagents. Suitable doses for a secondary agent are typically in the range of about 0.05 µg/day to about 500 mg/day.

Diseases and Conditions

The combination of (a) a PDE3/PDE4 inhibitor as defined herein and (b) a muscarinic receptor antagonist as defined herein is useful for treating a disease or condition which is based on (i) acute or chronic obstruction of vessels or bronchi or (ii) acute or chronic inflammation, in a subject in need thereof.

Typically, the disease or condition is selected from:

1. respiratory tract: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus;

2. bone and joints: arthritides associated with or including osteoarthritis/osteoarthrosis, both primary and secondary to, for example, congenital hip dysplasia; cervical and lumbar spondylitis, and low back and neck pain; rheumatoid arthritis and Still's disease; seronegative spondyloarthropathies including ankylosing spondylitis, psoriatic arthritis, reactive arthritis and undifferentiated spondarthropathy; septic arthritis and other infection-related arthopathies and bone disorders such as tuberculosis, including Potts' disease and Poncet's syndrome; acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositis and polymyositis; polymalgia rheumatica; juvenile arthritis including idiopathic inflammatory arthritides of whatever joint distribution and associated syndromes, and rheumatic fever and its systemic complications; vasculitides including giant cell arteritis, Takayasu's arteritis, Churg-Strauss syndrome, polyarteritis nodosa, microscopic polyarteritis, and vasculitides associated with viral infection, hypersensitivity reactions, cryoglobulins, and paraproteins; low back pain; Familial Mediterranean fever, Muckle-Wells syndrome, and Familial Hibernian Fever, Kikuchi disease; drug-induced arthalgias, tendonititides, and myopathies;

3. pain and connective tissue remodelling of musculo-skeletal disorders due to injury [for example sports injury] or disease: arthitides (for example rheumatoid arthritis, osteoarthritis, gout or crystal arthropathy), other joint disease (such as intervertebral disc degeneration or temporo-mandibular joint degeneration), bone remodelling disease (such as osteoporosis, Paget's disease or osteonecrosis), polychondritits, scleroderma, mixed connective tissue disorder, spondyloarthropathies or periodontal disease (such as periodontitis);

4. skin: psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous, eosinophilias, alopecia areata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions;

5. eyes: blepharitis; conjunctivitis, including perennial and vernal allergic conjunctivitis; iritis; anterior and posterior uveitis; choroiditis; autoimmune; degenerative or inflammatory disorders affecting the retina; ophthalmitis including sympathetic ophthalmitis; sarcoidosis; infections including viral, fungal, and bacterial;

6. gastrointestinal tract: glossitis, gingivitis, periodontitis; oesophagitis, including reflux; eosinophilic gastro-enteritis, mastocytosis, Crohn's disease, colitis including ulcerative colitis, proctitis, pruritis ani; coeliac disease, irritable bowel syndrome, and food-related allergies which may have effects remote from the gut (for example migraine, rhinitis or eczema);

7. abdominal: hepatitis, including autoimmune, alcoholic and viral; fibrosis and cirrhosis of the liver; cholecystitis; pancreatitis, both acute and chronic;

8. genitourinary: nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female);

9. allograft rejection: acute and chronic following, for example, transplantation of kidney, heart, liver, lung, bone marrow, skin or cornea or following blood transfusion; or chronic graft versus host disease;

10. CNS: Alzheimer's disease and other dementing disorders including CJD and nvCJD; amyloidosis; multiple sclerosis and other demyelinating syndromes; cerebral atherosclerosis and vasculitis; temporal arteritis; myasthenia gravis; acute and chronic pain (acute, intermittent or persistent, whether of central or peripheral origin) including visceral pain, headache, migraine, trigeminal neuralgia, atypical facial pain, joint and bone pain, pain arising from cancer and tumor invasion, neuropathic pain syndromes including diabetic, post-herpetic, and HIV-associated neuropathies; neurosarcoidosis; central and peripheral nervous system complications of malignant, infectious or autoimmune processes;

11. other auto-immune and allergic disorders including Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome;

12. other disorders with an inflammatory or immunological component; including acquired immune deficiency syndrome (AIDS), leprosy, Sezary syndrome, and paraneoplastic syndromes;

13. cardiovascular: atherosclerosis, affecting the coronary and peripheral circulation; pericarditis; myocarditis, inflammatory and auto-immune cardiomyopathies including myocardial sarcoid; ischaemic reperfusion injuries; endocarditis, valvulitis, and aortitis including infective (for example syphilitic); vasculitides; disorders of the proximal and peripheral veins including phlebitis and thrombosis, including deep vein thrombosis and complications of varicose veins;

14. oncology: treatment of common cancers including prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes; and, 15. gastrointestinal tract: Coeliac disease, proctitis, eosinopilic gastro-enteritis, mastocytosis, Crohn's disease, ulcerative colitis, microscopic colitis, indeterminant colitis, irritable bowel disorder, irritable bowel syndrome, non-inflammatory diarrhea, food-related allergies which have effects remote from the gut, e.g., migraine, rhinitis and eczema.

Preferably, the disease or condition is asthma, allergic asthma, hay fever, allergic rhinitis, bronchitis, emphysema, bronchiectasis, chronic obstructive pulmonary disease (COPD), adult respiratory distress syndrome (ARDS), steroid resistant asthma, severe asthma, paediatric asthma, cystic fibrosis, lung fibrosis, pulmonary fibrosis, interstitial lung disease, skin disorders, atopic dermatitis, psoriasis, ocular inflammation, cerebral ischaemia, or auto-immune diseases.

More preferably, the disease or condition is asthma or chronic obstructive pulmonary disease (COPD).

The subject treated is typically a human.

Typically, the active components (a) and (b) are co-administered. Preferably, the active components (a) and (b) are contained in a single dosage form.

Alternatively, active components (a) and (b) may be administered separately. There may be a time delay between the administration of the active components (a) and (b).

The active components (a) and (b) may be administered by inhalation. The active components (a) and (b) may be administered by aerosol.

The amount of active agent administered per dose or the total amount administered per day may be predetermined or it may be determined on an individual patient basis by taking into consideration numerous factors, including the nature and severity of the patient's condition, the condition being treated, the age, weight, and general health of the patient, the tolerance of the patient to the active agent, the route of administration, pharmacological considerations such as the activity, efficacy, pharmacokinetics and toxicology profiles of the active agent and any secondary agents being administered, and the like. Treatment of a patient suffering from a disease or medical condition (such as COPD) can begin with a predetermined dosage or a dosage determined by the treating physician, and will continue for a period of time necessary to prevent, ameliorate, suppress, or alleviate the symptoms of the disease or medical condition. Patients undergoing such treatment will typically be monitored on a routine basis to determine the effectiveness of therapy. For example, in treating COPD, significant improvement in forced expiratory volume (measured in one second) may be used to determine the effectiveness of treatment. Similar indicators for the other diseases and conditions described herein, are well-known to those skilled in the art, and are readily available to the treating physician. Continuous monitoring by the physician will insure that the optimal amount of active agent will be administered at any given time, as well as facilitating the determination of the duration of treatment. This is of particular value when secondary agents are also being administered, as their selection, dosage, and duration of therapy may also require adjustment. In this way, the treatment regimen and dosing schedule can be adjusted over the course of therapy so that the lowest amount of active agent that exhibits the desired effectiveness is administered and, further, that administration is continued only so long as is necessary to successfully treat the disease or medical condition. Accordingly, in one embodiment, compositions of the invention are useful for treating smooth muscle disorders in mammals, including humans and their companion animals (e.g., dogs, cats etc.). Such smooth muscle disorders include, by way of illustration, overactive bladder, chronic obstructive pulmonary disease and irritable bowel syndrome. Typically, suitable doses for treating smooth muscle disorders or other disorders mediated by muscarinic receptors will range from about 0.14 µg/kg/day to about 7 mg/kg/day of active agent; including from about 0.15 µg/kg/day to about 5 mg/kg/day. For an average 70 kg human, this would amount to about 10 µg per day to about 500 mg per day of active agent.

Typically, compositions of the invention are useful for treating pulmonary or respiratory disorders, such as COPD or asthma, in mammals including humans, by administering to a patient a therapeutically effective amount of the composition. Generally, the dose for treating a pulmonary disorder will range from about 10-1500 µg/day. The term "COPD" is understood by those of ordinary skill in the art to include a variety of respiratory conditions, including chronic obstructive bronchitis and emphysema, as exemplified by the teachings of Barnes (2000) N. Engl. J. Med. 343:269-78, and references cited therein.

When administered by inhalation, compositions of the invention typically have the effect of producing bronchodilation. Accordingly, in another of its method aspects, the invention is directed to a method of producing bronchodilation in a patient, comprising administering to a patient a bronchodilation-producing amount of a composition of the invention. Generally, the therapeutically effective dose for producing bronchodilation will range from about 10-1500 µg/day.

Alternatively, compositions of the invention may be used to treat overactive bladder. When used to treat overactive bladder, a typical dose will range from about 1.0-500 mg/day. Alternatively, compositions of the invention may be used to treat irritable bowel syndrome. When used to treat irritable bowel syndrome, compositions of the invention will typically be administered orally or rectally, and a typical dose will range from about 1.0-500 mg/day.

It is a finding of the invention, following safety studies, that RPL554 does not interact adversely with muscarinic receptor antagonists (such as atropine) with respect to blood pressure or heart rate. Likewise, the cardiovascular effects of muscarinic receptor antagonists (such as atropine) are not affected by RPL554.

The following Examples illustrate the invention.

EXAMPLES

Example 1

Material and Methods
Preparation of Tissues

Regions of macroscopically normal lungs were taken from uninvolved areas resected from 24 subjects (11 male and 13 female, 60.1±1.6 years old) undergoing lobectomy surgery for lung cancer, but without a history of chronic airway disease.

Airways were immediately placed into oxygenated Krebs-Henseleit buffer solution (KH) (mM: NaCl 119.0, KCl 5.4, CaCl$_2$ 2.5, KH$_2$PO$_4$ 1.2, MgSO$_4$ 1.2, NaHCO$_3$ 25.0, glucose 11.7; pH 7.4) containing the cyclooxygenase (COX) inhibitor indomethacin (5.0 µM), and transported at 4° C. from the "Regina Elena National Cancer Institute" or the "Sant' Andrea Hospital" to the Respiratory Research Laboratory in the Surgery and Medicine Faculty of "Tor Vergata University", Rome, Italy. None of the subjects were chronically treated with theophylline, β$_2$-agonists or glucocorticosteroids. Serum IgE levels determined on the day of surgery were in the normal range. Preoperative lung function parameters were generally normal and there were no signs of respiratory infections.

In the laboratory, airways were dissected from connective and alveolar tissues. Then, segmental bronchi were isolated and stored overnight in KH buffer solution at refrigeration temperature. The next morning, bronchi were cut into rings (n=120; thickness: 1-2 mm; diameter: 5-7 mm) and transferred into 4400 four-chamber 10 ml Isolated Organ Baths (Ugo Basile, VA—Italy) containing KH buffer (37° C.) and continuously aerated with a 95:5% mixture of $O_2/CO_2$.

Preparation of Drugs

The following drugs were used: acetylcholine, histamine, atropine, papaverine and indomethacin. All substances were obtained from Sigma-Aldrich (St. Louis, USA). Drugs were dissolved in distilled water except for indomethacin and quinine, which were dissolved in ethanol and then diluted in a KH buffer. The maximal amount of ethanol (0.02%) did not influence isolated tissue responses (Freas et al., 1989; Hatake and Wakabayashi, 2000). RPL554 was kindly provided by Verona Pharma PLC, London, UK. Compounds were stored in small aliquots at −80° C. until their use.

Tension Measurement

Human bronchi were placed in organ baths containing KH buffer solution (37° C.) medicated with indomethacin (5.0 µM), bubbled with 95% $O_2$/5% $CO_2$ and suspended under passive tension (0.5-1.0 g). Bronchial rings were mounted on hooks in the organ baths where one hook was attached with threaded to a stationary rod and the other hook tied with thread to an isometric force displacement transducer. Airways were allowed to equilibrate for 90 min with repeated changes of the medicated KH buffer solution every 10 min. Changes in isometric tension were measured with a transducer (Fort 10 WPI, Basile, Instruments, Italy) and the tissue responsiveness was assessed by acetylcholine (100 µM); when the response reached a plateau, rings were washed three times and allowed to equilibrate for 45 min.

Study Design

Influence of RPL554 on Electrical Field Stimulation

Each organ bath was fitted with two platinum plate electrodes (1 cm$^2$) placed alongside the tissue (10 mm apart) for electrical field stimulation (EFS). Experiments were performed using trains of 10 Hz EFS (biphasic pulse with a constant current of 10V, 0.5 ms, 10 s), one pulse every 5 min for the first hour and then at 30 min intervals for the next 5 hours by a 3165 multiplexing pulse booster (Ugo Basile, VA—Italy) (Binks et al., 2001). After the start of the EFS trains, tissues were incubated with RPL554 (10 or 100 µM) until maximum inhibition of the contractile response to electrical field stimulation (EFS) was achieved. Incubation with drug was then terminated and the tissues repeatedly washed over a 30 min period and then once every 30 min up to 5 h post drug administration.

Relaxant Effect of RPL554 on Passively Sensitized Bronchi

Human isolated bronchial rings were rotated overnight at room temperature in tubes containing KH buffer solution in the absence (non-sensitized control rings) or the presence of 10% vol$^{-1}$ sensitizing serum (sensitized rings) as described elsewhere (Watson et al., 1997; Rabe, 1998). Subjects suffering from atopic asthma (total IgE>250 U ml$^{-1}$ specific against common aeroallergens) during exacerbation provided signed consent for serum donation. Sera was prepared by centrifugation of whole blood and sera samples were frozen at −80° C. in 200 ml aliquots until required.

The next morning, after removal of adhering alveolar and connective tissues, bronchial rings were transferred into an organ bath containing KH buffer (37° C.) and continuously gassed with a 95% O2/5% CO2. Tissues were pre-incubated for 30 min with RPL554 (1, 10 and 100 µM) and then followed (without washing) by the construction of concentration responses curve to histamine (10 nM-1 mM) in the presence of RPL554.

Synergistic Effect of RPL554 Plus Muscarinic Receptor Antagonist

To test the possible synergistic relaxation induced by RPL554 in combination with a muscarinic receptor antagonist, the bronchialrings were contracted with acetylcholine at the concentration required to cause a 70% maximal effect (EC70) and allowed a 15 min stabilization period. Then, concentration response curves were constructed to test individual compound RPL554 and muscarinic receptor antagonist alone; as well as RPL554 administered in combination with a muscarinic receptor antagonist in order to produce isobolar graphs as described elsewhere (Greco et al., 1995; Tallarida, 2001; Goldoni and Johansson, 2007; Boik et al., 2008; Lee, 2010).

Intervals of 20 min between successive concentrations were used to reach a stable level of relaxation before the administration of the next concentration. At the completion of the experiment, papaverine (500 µM) was added to relax the tissues completely and provide a standard to which the relaxation of each tissue could be compared.

Analysis of Results

Analysis of EFS Studies

Bronchial contractile tension induced by EFS was measured as a percentage of control bronchi, and polynomial curves were constructed by fitting models of biological data using nonlinear regression as described elsewhere (Motulsky and Christopoulos, 2004). The maximal effect (Emax) was identified as the lowest contractile force induced by EFS stimulation and the offset ($t_{1/2}$, min) indicates the time to evoke a half of maximal relaxation. For every three bronchial rings mounted in the isolated organ bath system, one was used as a time control as described elsewhere (Mercier et al., 2002).

Analysis of Concentration Response Studies

Appropriate curve-fitting to a sigmoidal model was used to calculate the effect (E), the Emax and the concentration required to cause a 50% maximal effect (EC50). The equation used was log [agonist] vs. response, Variable slope, expressed as $Y=Bottom+(Top-Bottom)/\{1+10^{\wedge}[(Log\ EC50-X)*HillSlope]\}$ (Motulsky and Christopoulos, 2004; Goodman et al., 2008). E/Emax was expressed as percentage of Emax elicited by the contractile agents; EC50 values were converted to $pD_2$ for statistical analysis (Goodman et al., 2008) and the relaxant responses were expressed as a percentage of papaverine (500 µM) induced relaxation.

Analysis of Synergism Studies

The analysis of the potential synergism between RPL554 plus muscarinic receptor antagonist was measured by applying the Berenbaum method, the Bliss Independence (BI) criterion and the Loewe Additivity (LA) model through curved isoboles (Berenbaum, 1977; Greco et al., 1995; Grabovsky and Tallarida, 2004; Tallarida, 2006; Goldoni and Johansson, 2007; Tallarida and Raffa, 2010).

In order to apply the Berenbaum method, the Interaction Index for the EC50 values was evaluated and, therefore, if the Interaction Index was <1 the effect was considered synergistic; if the Interaction Index was >1 the effect was antagonistic and if the Interaction Index was=0 the effect was considered additive (Goldoni and Johansson, 2007; Lee, 2010).

The BI theory for two agents is expressed by the following equation: $E(x,y)=Ex+Ey-(Ex*Ey)$, where E is the fractional effect, and x and y are the concentrations of two compounds in a combination experiment. If the combination effect is higher than the expected value from the above equation, the interaction is considered synergistic, while if this effect is lower, the interaction is antagonistic. Otherwise, the effect is additive and there is no interaction (Greco et al., 1995; Meletiadis et al., 2003; Boucher and Tam, 2006; Goldoni and Johansson, 2007; Boik et al., 2008; Lee, 2010).

In this study, the BI equation was characterized by X=RPL554 and Y=muscarinic receptor antagonist.

Control concentration response curves for atropine and RPL554 from bronchi from each lung were fitted to a 4 parameter logistic equation to calculate parameter estimates of Emax, slope (nH) and potency (EC50). The following parameter estimates Emax and nH (mean±SD) and EC50 (geomean, 95% CI) for atropine (66±14, 0.912±0.488, 1.181 (0.134–10.4) μM, n=5, respectively) and RPL554 (100±0, 2.271±0.713, 21.2 (11.5–39.1) μM, n=5, respectively) were then used to calculate the additive response for each drug pair combination to evaluate synergism (Tallarida and Raffa 2010)(Grabovsky and Tallarida 2004). Using the concept of dose equivalence, the relationship a/A+b/B=1 was reformulated as b+beq (a)=B, where beq is the dose equivalent of a and solving for beq(a) by equating the two individual concentration response curves $E_A$=f(A) and $E_B$=f(B). The additive response ($E_{ab}$) for each dose combination with respect to B was then calculated by insertion of B into $E_B$=f(B). The difference between the observed relaxation response to the combination doses and the additive response was calculated and analysed using a one sample t-test and for multiple comparisons, the probability was adjusted for multiple comparisons using a Bonferroni correction. For illustrative purposes, the 1:1 dose combinations were analysed for synergy.

Statistical Analysis

All values are presented as mean±SEM for each treatment group. Statistical significance was assessed by Student's t test or analysis of variance (ANOVA) if required and the level of statistical significance was defined as P<0.05 (Motulsky, 1995). All data analyses were performed using computer software (GraphPad Prism, San Diego Calif. USA; Microsoft Excel, Redmond Wash. USA).

Synergistic Effect of RPL554 Administered in Combination with Atropine (a Muscarinic Receptor Antagonist)

To test the synergistic relaxation induced by RPL554 administered in combination with atropine, the bronchial rings were contracted with acetylcholine at the concentration required to cause a 70% maximal effect (EC70) and allowed a 15 min stabilization period. Then, concentration response curves were constructed to test individual compound RPL554, or atropine alone; or RPL554 administered in combination with atropine in order to produce isobolar graphs (atropine:RPL554 and ranging from 10:1 to 1:100) as described elsewhere (Greco et al., 1995; Tallarida, 2001; Goldoni and Johansson, 2007; Boik et al., 2008; Lee, 2010).

Intervals of 20 min between successive concentrations were used to reach a stable level of relaxation before the administration of the next concentration. At the completion of the experiment, papaverine (500 μM) was added to relax the tissues completely and provide a standard to which the relaxation of each tissue could be compared.

Results

Baseline Characteristics of Bronchial Rings

There were no significant differences (P>0.05) between the baseline characteristics of the human isolated bronchial rings employed in the study concerning the wet weight (220.5±16.5 mg), the contraction induced by acetylcholine (100 μM) (440±95 mg) and the contraction induced by EFS (10 Hz) before treatments with drugs (445±98 mg).

In preliminary experiments, a concentration response curve to acetylcholine (from 1 nM to 1 mM) was constructed to establish a sub-maximal response (approximately 70% maximum response; 1250±190 mg; n=5) for subsequent studies.

Influence of RPL554 on Bronchial Tone of Isolated Human Airways

RPL554 inhibited the contractile response induced by EFS of human bronchial tissues that was maintained for at least 5 h after exposure to this drug (FIG. 1). RPL554 abolished these contractile responses at a maximum concentration of 100 μM (Emax 91.33±3.37%; $T_{1/2}$23.7±12.3 min).

Figure 2:
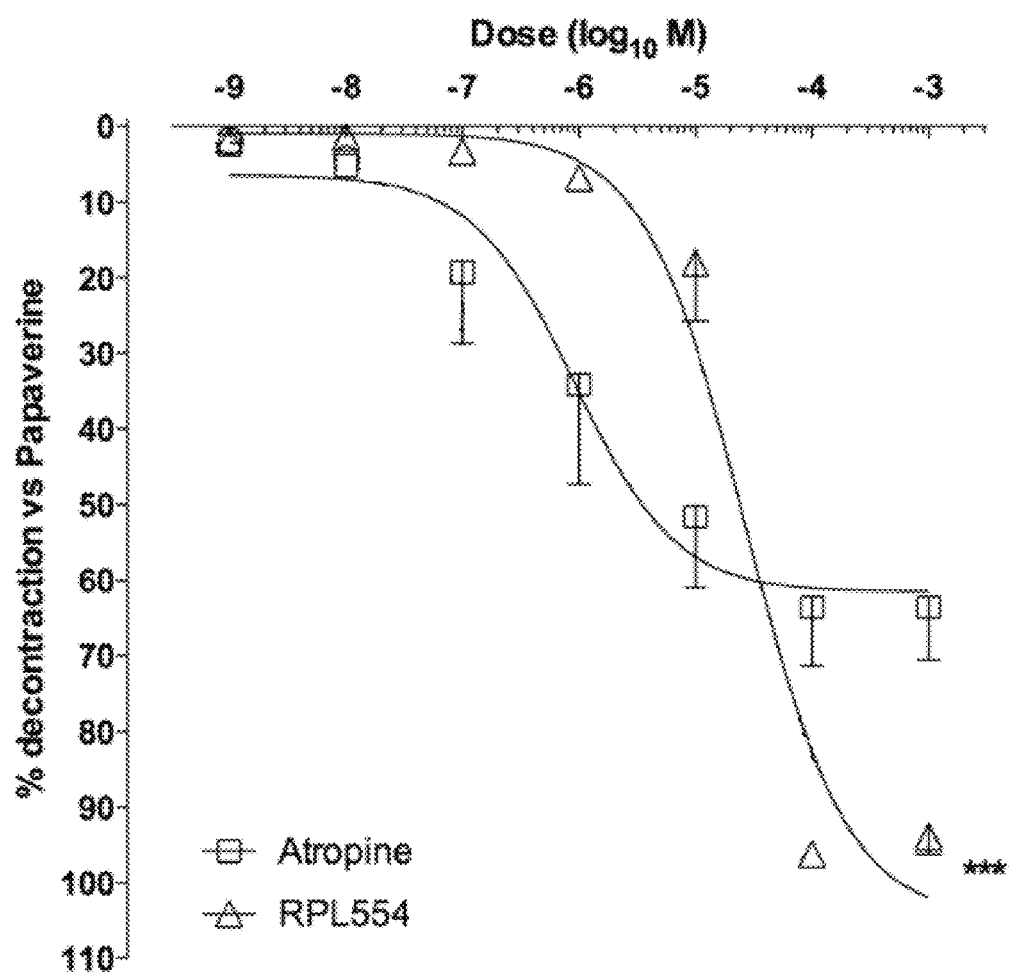
FIG. 2: Human bronchial relaxation of RPL554 and atropine on sub-maximal contraction by acetylcholine. Points shown are from experiments performed with samples of n=5 different subjects and they are represented as mean±SEM; ***P<0.001 vs atropine.

RPL554 caused a concentration-dependent relaxation of human isolated bronchial tissues pre-contracted with acetylcholine. RPL554 was less potent (P<0.05) than atropine in bronchial relaxation but, in contrast to atropine, RPL554 completely relaxed tissues (P<0.001). Control concentration response curves for atropine and RPL554 from bronchi from each lung were fitted to a 4 parameter logistic equation to calculate parameter estimates of Emax, slope (nH) and potency (EC50). The following parameter estimates Emax and nH (mean±SD) and EC50 (geomean, 95% CI) for atropine (66±14, 0.912±0.488, 1.181 (0.134–10.4) μM, n=5, respectively) and RPL554 (100±0, 2.271±0.713, 21.2 (11.5–39.1) μM, n=5, respectively) (FIG. 2).

Figure 3:
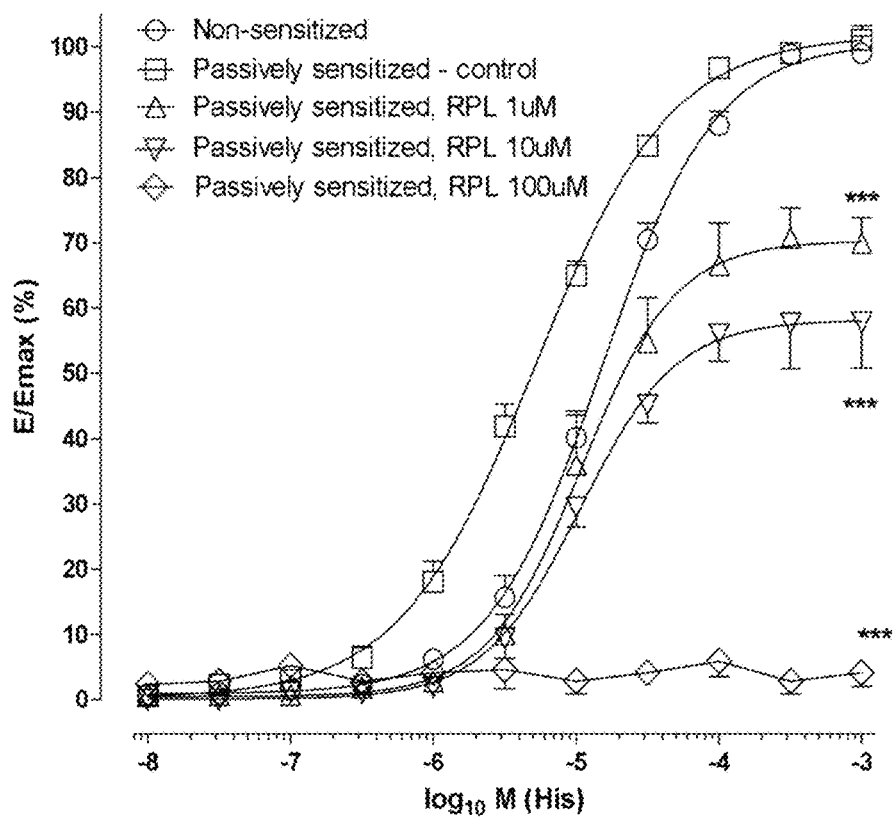
FIG. 3: Effect of increasing dose of RPL554 on contractile effect of histamine in passively sensitized human isolated bronchi. Points shown are from experiments performed with samples of n=5 different subjects and they are represented as mean±SEM ***P<0.001 vs passively sensitized control.

The passive sensitization of bronchi enhanced the contractile effect of histamine compared to non-sensitized tissues. In passively sensitized bronchi, RPL554 at 1 and 10 μM significantly (P<0.001) shifted leftward the concentration response curve to histamine compared with untreated tissues and RPL554 at 100 μM completely abolished the contraction induced by histamine (FIG. 3, Table 1).

TABLE 1

Effect of RPL554 on contraction induced by histamine in passively sensitized bronchi. Data shown are from experiments performed with samples of n = 5 different subjects and they are represented as mean ± SEM

|  | Non-sensitized | Passively sensitized | | |
| --- | --- | --- | --- | --- |
|  |  | Control | RPL554 1 uM | RPL554 10 uM | RPL554 100 uM |
| Emax | 100.7 ± 1.7 | 101.8 ± 1.4 | 70.3 ± 2.7*** | 58.1 ± 2.2*** | nd |
| pD2 | 4.82 ± 0.03*** | 5.29 ± 0.03 | 4.97 ± 0.07*** | 4.98 ± 0.07*** | nd |

***P < 0.001 vs passively sensitized control.

Synergistic Relaxant Effect of RPL554 Plus Atropine on Human Bronchial Tone

Figure 4:
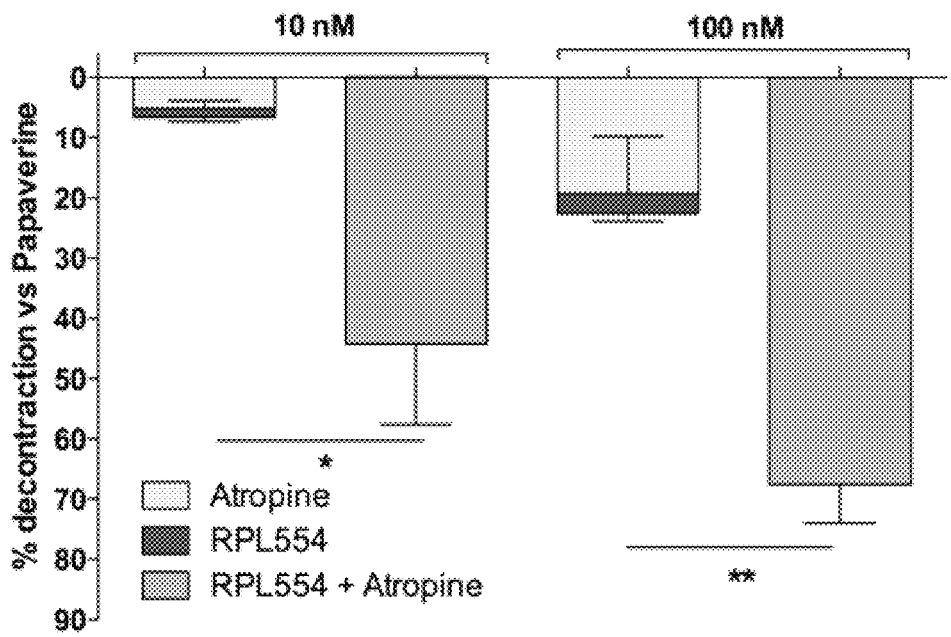
FIG. 4: Low concentrations interaction (10 nM and 100 nM) between atropine and RPL554. Data are from experiments performed with samples of n=5 different subjects and they are represented as mean±SEM. *P<0.05 and **P<0.01.

The interaction of RPL554 plus atropine produced a significant synergistic effect of RPL554 over the concentration range of 1 nM to 10 μM (1 nM: P<0.05; 10 nM and 1 μM: P<0.01; 100 nM and 10 μM: P<0.001) and the maximal synergism was detected for the crossing concentrations of RPL554 1 μM and atropine 10 nM (BI delta effect: 0.54±0.09). Lower concentrations of RPL554 and atropine interacted synergistically (10 nM, P<0.05 and 100 nM, P<0.01) by increasing the relaxation of bronchial rings by ≈ 4.85 fold, compared to the sum of effects induced by each drug given alone (FIG. 4).

The results of the isomolar association (1:1) of RPL554 plus atropine on human bronchial tone pre-contracted with acetylcholine indicated a statistically significant BI interaction (P<0.01), based on the enhancement of the relaxant potency (Table 2).

TABLE 2

Relaxant synergistic effect of RPL554 plus atropine (isomolar, 1:1) on submaximal contraction induced by acetylcholine. Data shown are from experiments performed with samples of n = 5 different subjects and they are represented as mean ± SEM.

| | RPL554 + atropine | |
|---|---|---|
| | Observed | Expected |
| Emax | 97.87 ± 1.50 | 98.68 ± 7.91 |
| pD2 | 7.54 ± 0.31 | 5.55 ± 0.33 |
| Delta potency (observed-expected) | 1.99 ± 0.10** | |

**P < 0.01 for zero-interaction hypothesis delta effect (observed vs expected values).

Figure 6:
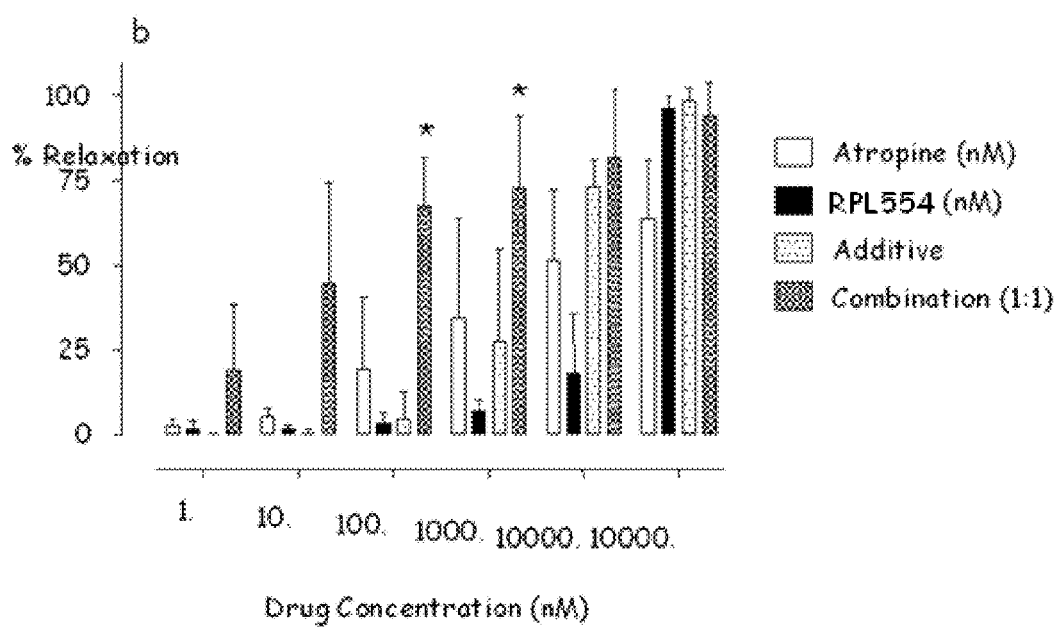
FIG. 6: Bar graph representing the relaxation response to atropine (open column; Atropine, nM), RPL554 (closed column; nM) the additive response of each dose combination (stippled column; Additive) and the observed relaxation response for each dose combination (dark stippled column; Combination 1:1)). The concentrations of each agonist are shown on the X axis. Each bar represents the mean and vertical lines represent the standard deviation (N=5). In the case of the additive response, the SD was estimated using the methods of Tallarida and Raffa (2010). * P<0.05 (adjusted) cf additive response using a one sample t-test.
Figure 7:
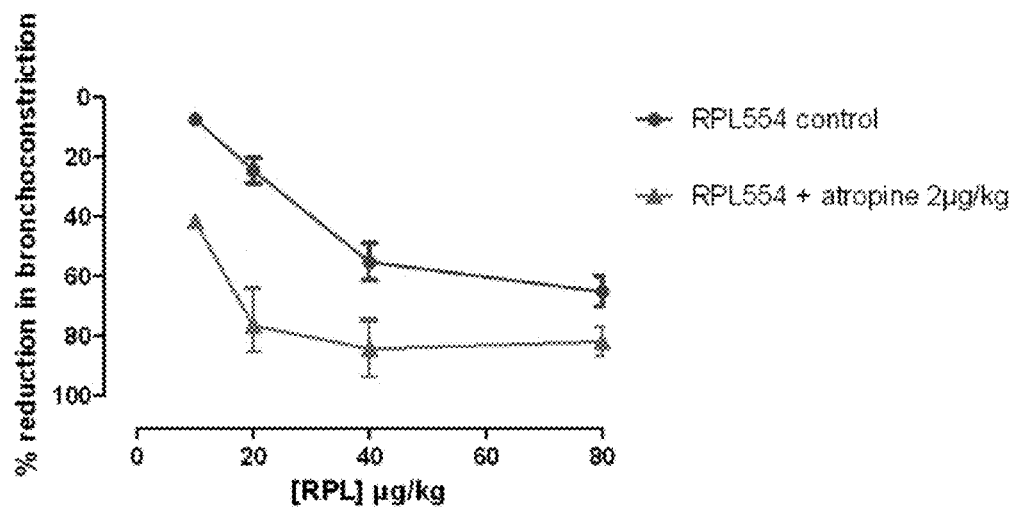
FIG. 7: Reduction in airways obstruction (induced by the intravenous (iv.) administration of bombesin (2 μg/ml; 5 ml/hr)) following the iv. administration of RPL554 alone (●) or in combination with 2 μg/kg atropine (▲).
Figure 8:
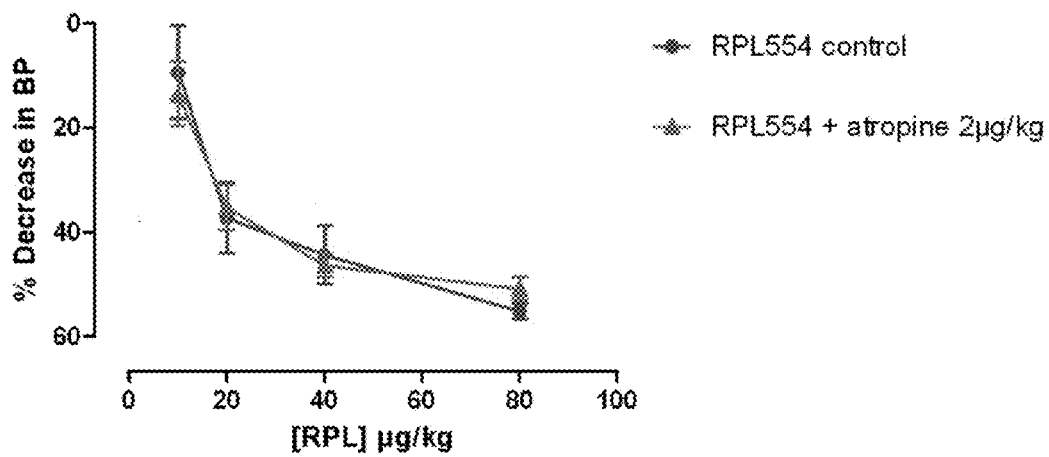
FIG. 8: Reduction in mean arterial blood pressure following the iv. administration of RPL554 alone (●) or in combination with 2 μg/kg atropine (▲).
Figure 9:
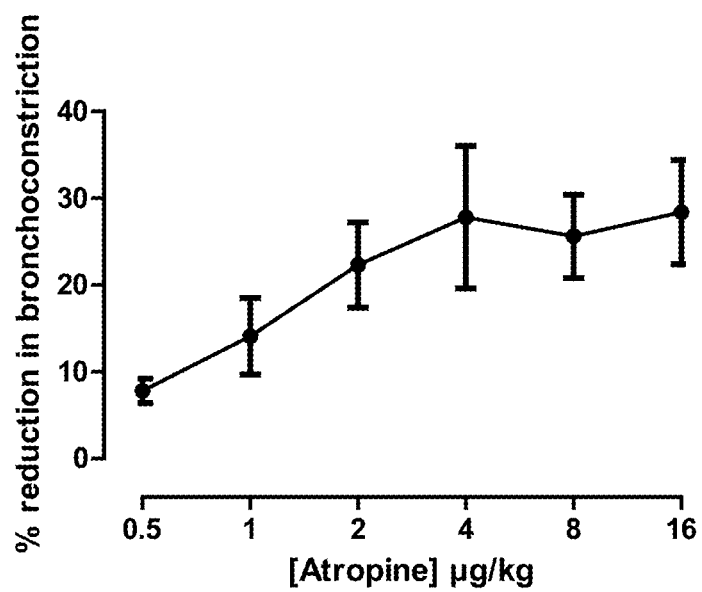
FIG. 9: Reduction in airways obstruction (induced by the intravenous (iv.) administration of bombesin (2 μg/ml; 5 ml/hr)) following the iv. administration of atropine.
Figure 10:
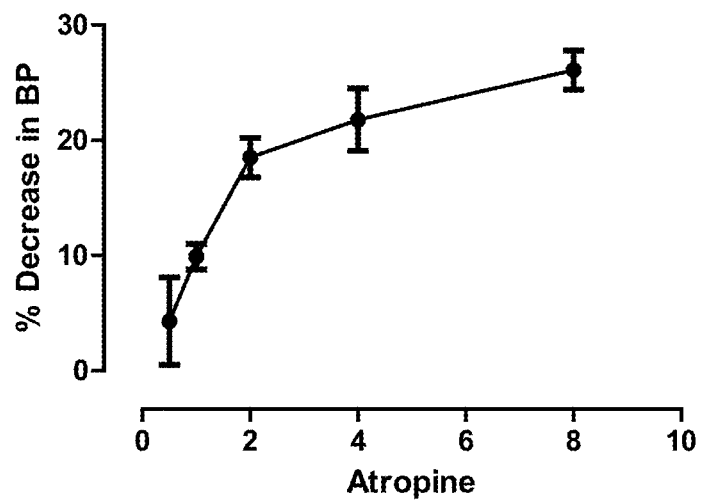
FIG. 10: Reduction in mean arterial blood pressure following the iv. administration of atropine.
Figure 11:
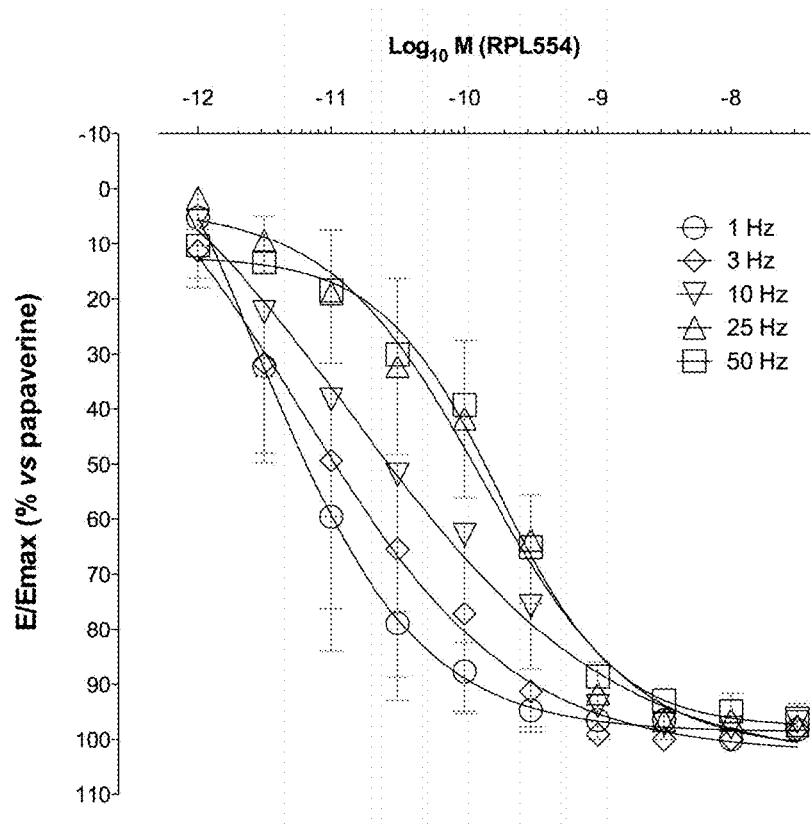
FIG. 11: Concentration response curve (CRC) of bronchial tone for glycopyrronium at different electrical field stimulation (EFS) frequencies.
Figure 12:
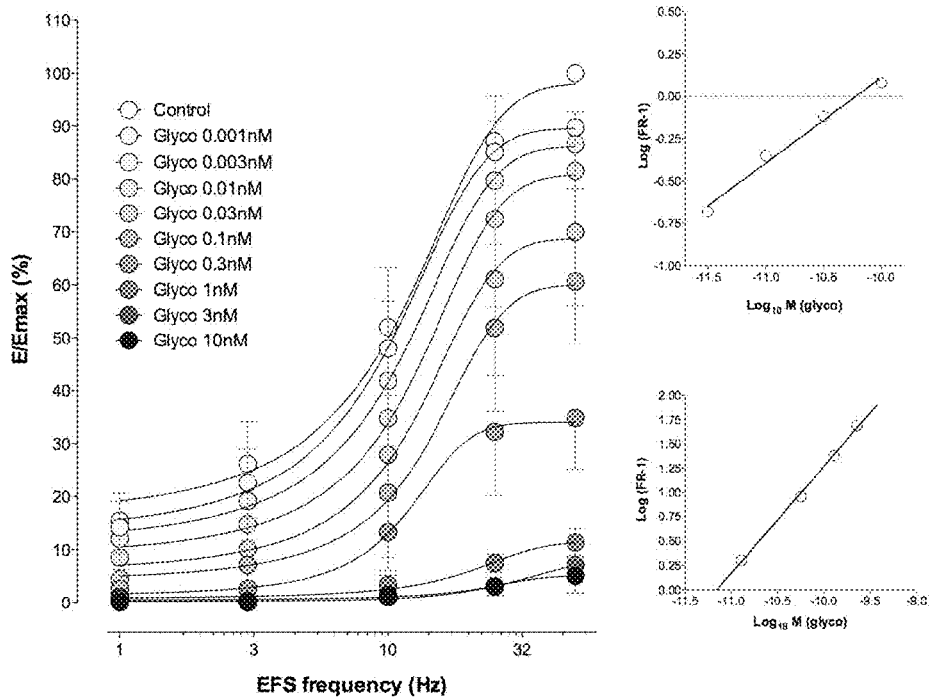
FIG. 12: Frequency response curve of bronchial tone for glycopyrronium at different concentrations of glycopyrronium as well as area under curve (AUC) plots.
Figure 13:
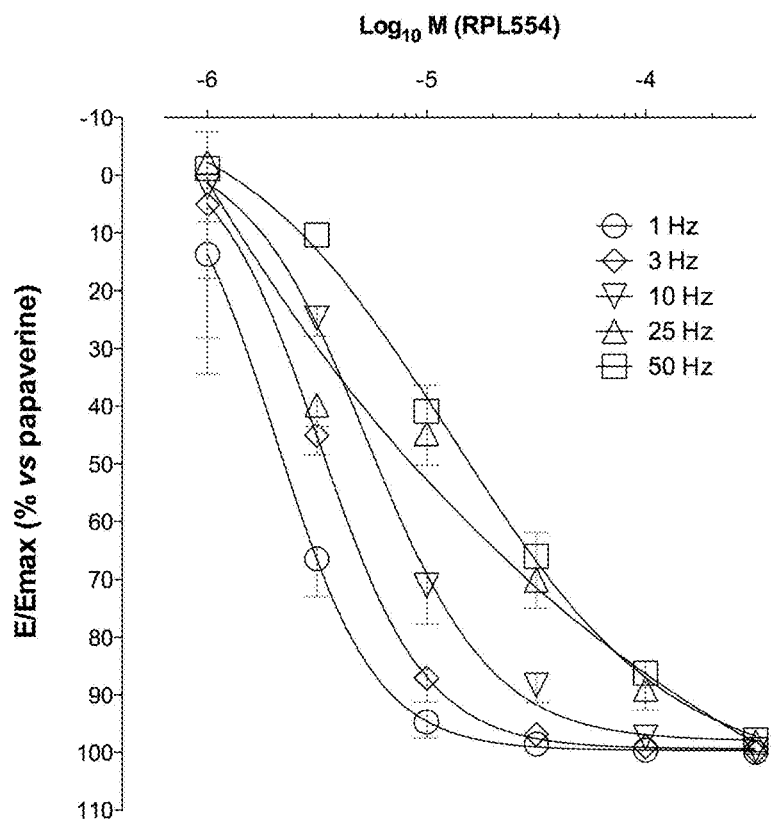
FIG. 13: Concentration response curve (CRC) of bronchial tone for RPL554 at different electrical field stimulation (EFS) frequencies.
Figure 14:
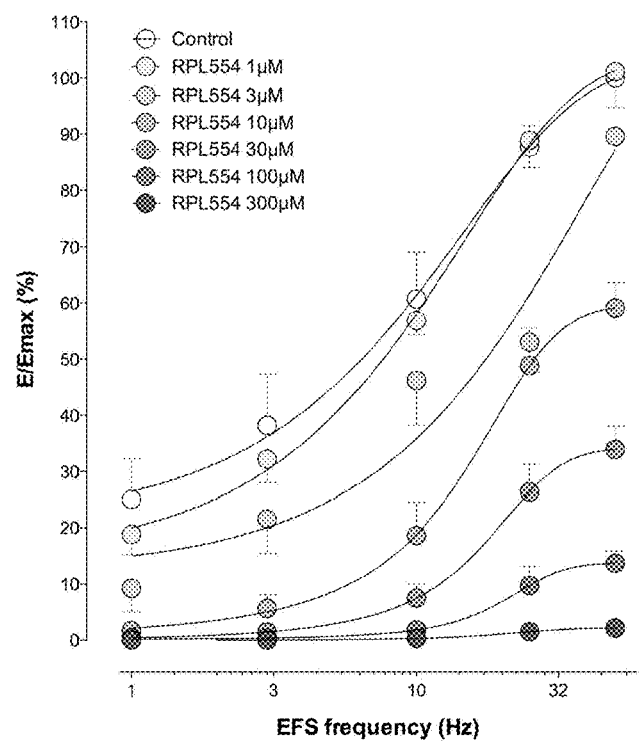
FIG. 14: Frequency response curve of bronchial tone for RPL554 at different concentrations.
Figure 15:
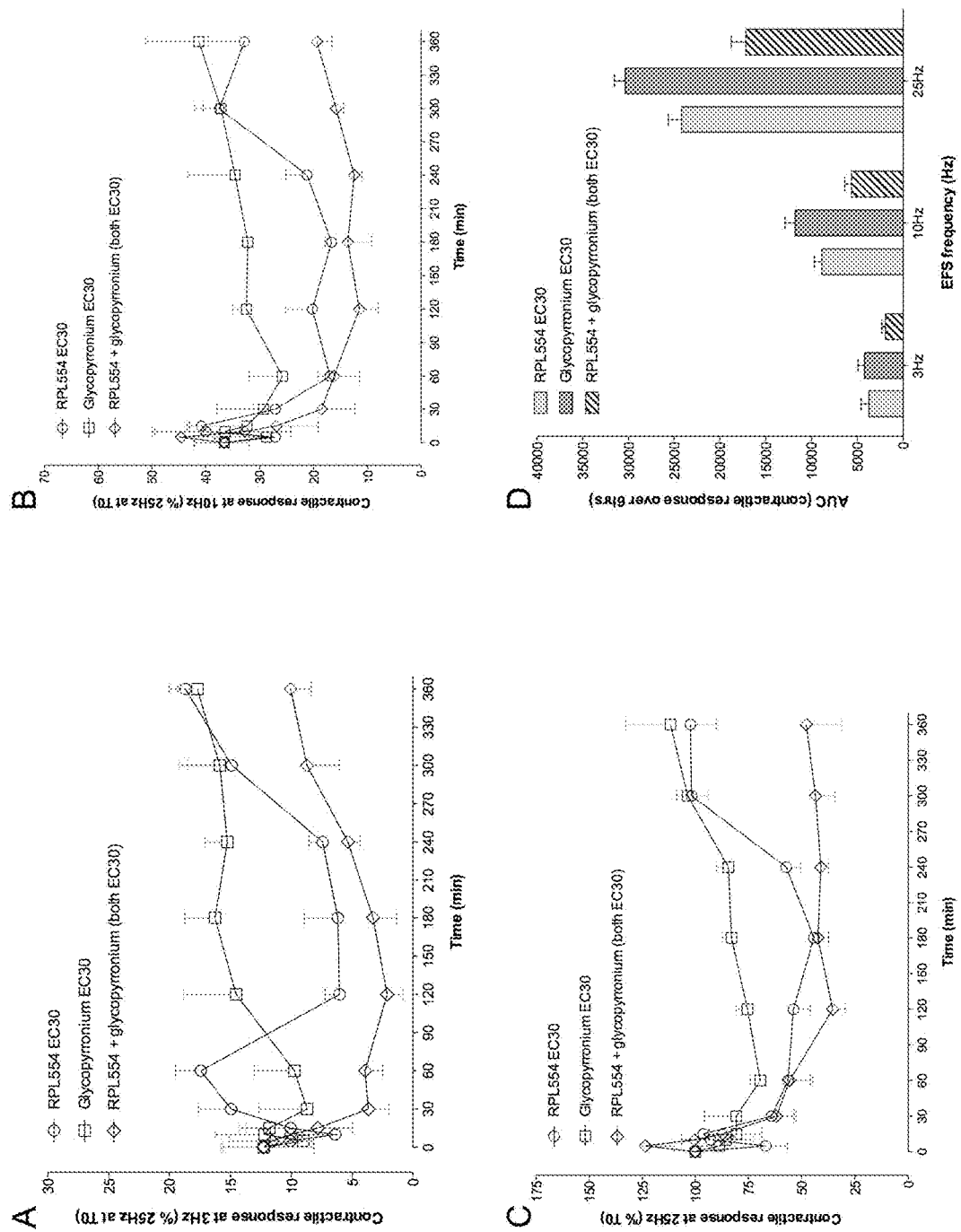
FIG. 15: Contractile response of human isolated bronchi for RPL554, glycopyrronium and RPL554 and glycopyrronium in combination at an EFS of (A) 3 Hz, (B) 10 Hz, and (C) 25 Hz, and AUC comparisons at each frequency (D).
Figure 16:
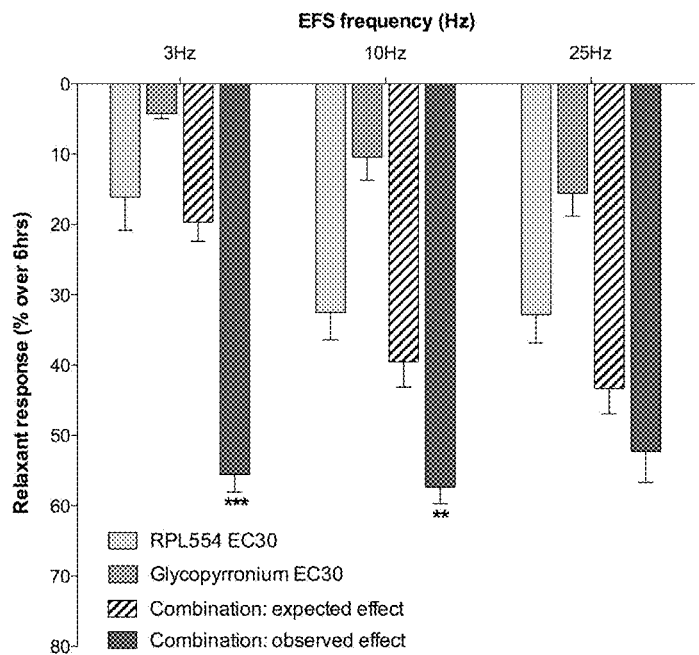
FIG. 16: Relaxant response for RPL554, glycopyrronium, expected response for RPL554 and glycopyrronium in combination and observed response for RPL554 and glycopyrronium in combination.

Furthermore, the Berenbaum analysis demonstrated that RPL554 plus atropine elicited synergistic interaction for RPL554 over the concentration range of 1 nM to 10 (Interaction Index: 0.09±0.07), and that RPL554 significantly caused a leftward shift of the relaxant concentration response curves to atropine of 2.91±0.44 logarithms (P<0.05). There was a statistical significant difference between the observed and additive relaxation response for the 1:1 dose combinations of atropine and RPL554 indicating evidence of synergy (FIG. 6).

Figure 5:
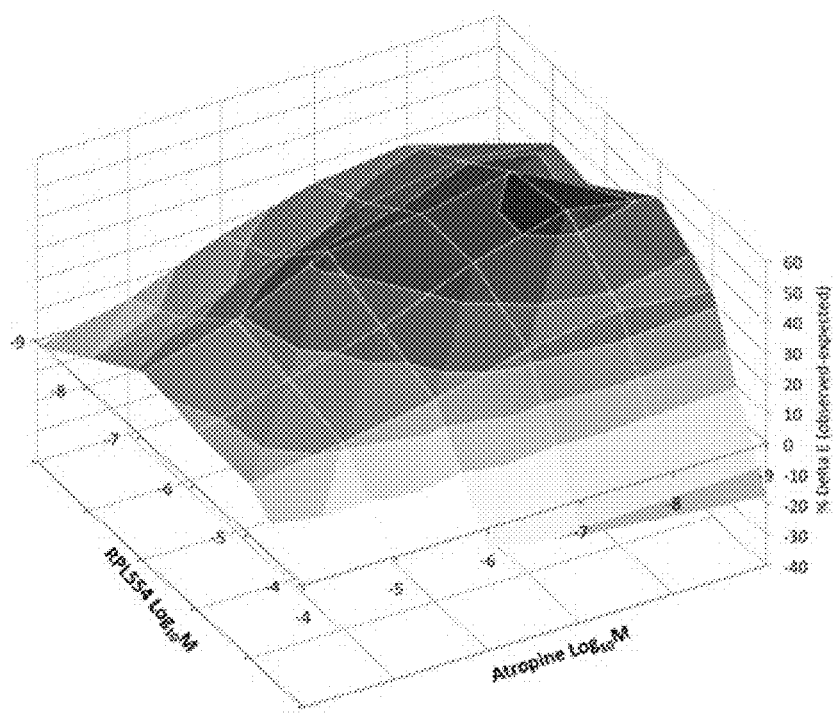
FIG. 5: Interaction surfaces obtained from response surface analysis of BI drug interaction model for the combination of RPL554 plus atropine. The horizontal-axis indicates the concentration of compounds and the vertical-axis represent the ΔE (relaxation, %). The 0-plane indicates BI interactions whereas the volume above the 0-plane represents synergistic (positive ΔE) interactions. The magnitude of interactions is directly related to ΔE and the different tones in the 3D plots represent different percentile bands of synergy (10%). Each point intersection represents the mean of experiments performed on samples from different subjects (n=5).

Finally, the 3D surface analysis using the BI method demonstrated that atropine induced a significantly high and wide synergistic interaction extended across all the concentrations when administered in association with RPL554 (FIG. 5).

It has been demonstrated that the selective inhibition of PDE3/PDE4 by RPL554 elicited relaxation of bronchial tone in human isolated airways which extends and supports observations previously reported in guinea-pig isolated trachea (Boswell-Smith et al., 2006b).

This inhibitory effect was maintained for up to 5 h after termination of drug exposure, confirming the long duration of action of this compound in human airways. Furthermore, RPL554 acted to relax airways contracted with either histamine or acetylcholine. Moreover, prior incubation of tissues with RPL554 resulted in a significant protection of the tissues against the contractile action of exogenously administered histamine in passively sensitized bronchi. In addition, the inhibition of PDE3/4 associated with a muscarinic receptor antagonist (atropine) demonstrated a synergistic effect on relaxation of ASM. These results show that RPL554 is a good functional antagonist against contractile agents in human bronchial tissues and when combined with a muscarinic receptor antagonist can have the ability to provide further synergistic bronchodilation.

RPL554 caused a concentration and time dependent inhibition of contractile responses elicited by EFS which had a considerably longer duration of action against EFS-induced contractile responses than other PDE4 inhibitors (Spina et al., 1998; Boswell-Smith et al., 2006b).

RPL554 was particularly effective at inhibiting the contractile response in passively sensitized human bronchi contracted with histamine and a variety of selective PDE3 and PDE4 inhibitors have been reported to significantly attenuate acute bronchospasm induced by antigen in sensitized guinea pigs (Boswell-Smith et al., 2006a).

RPL554 also induced a noticeable decrease in the maximum response to histamine in passively sensitized bronchi.

Safety Study of the Combination of the Present Invention

This study was undertaken to determine whether RPL554 has cardiovascular interactions with a muscarinic antagonist (atropine). A $\beta_2$ agonist (salbutamol) was included for completeness. RPL554 is a dual PDE3/PDE4 inhibitor being developed for treatment of chronic obstructive pulmonary disease (COPD) and asthma as an inhaled bronchodilator with possible anti-inflammatory actions. Cardiovascular responses to RPL554, salbutamol and atropine, given as intravenous bolus injection, were assessed as cardiovascular changes, measured as peak post-injection changes in blood pressure and heart rate. The study design was blind and random with drugs given as pairs five minutes apart in an alternating manner, e.g., RPL554 followed by salbutamol and vice versa. The doses chosen for study produced cardiovascular effects, and presumably plasma concentrations, much higher than those used for inhalation. Instead they were chosen to test for possible interactions under supra therapeutic conditions.

Summary

In this study, the effects of intravenously administered RPL554, salbutamol and atropine, alone and in combinations, were examined according to a randomized design, on blood pressure and heart rate in anaesthetized rats. Doses producing a 15-30 mmHg increase in mean blood pressure (MBP) and 30-60 beats per minute increase in heart rate (HR) were chosen from an initial dose-response study for RPL554 and salbutamol. For atropine, which produced lesser effects on blood pressure or heart rate, the maximum dose administered was chosen for further study. Thereafter, the chosen doses were examined in pairs administered 5 minutes part. The data from the study suggest that there was no interaction in cardiovascular terms between RPL554 and salbutamol, or between RPL554 and atropine in terms of effects on MBP or HR in anaesthetized rats. In order to rigorously test for possible interactions, the doses and route of administration chosen for study produced cardiovascular effects not seen with the usual therapeutic doses. In addition, the bolus intravenous route presumably resulted in much higher plasma concentrations than those not seen with the lower therapeutic doses given by inhalation. The intention of the study was to use supra normal conditions in order to challenge for possible interactions under supra therapeutic conditions.

Protocol

The studies were performed on Sprague-Dawley male rats from Charles River weighing 200-250 grms. Once the rats had been delivered to the experimental laboratory they did not have access to food and water for 1-3 hours. For the purposes of the experiment the animals were anaesthetized with thiobutabarbital at a dose of 100 mg/kg given by the i.p. route. There was no necessity for supplemental anaesthesia and at the end of the experimental period each rat was sacrificed. The study had two parts: (I) an initial dose ranging study and (II) the interaction study. The drugs studied were: RPL554 (R), salbutamol (S), atropine (A) all dissolved in saline.

(I) Initial Dose-Ranging Study

An initial dose-ranging study was performed as follows: cumulative dose-response curves for intravenous bolus doses of the three drugs were performed to determine appropriate doses of each of the three drugs for the full study. Doses of RPL554 or salbutamol producing a 15-30 mmHg increase in mean blood pressure (MBP) and 30-60 beats per minute increase in heart rate (HR) were chosen from this initial dose-response study. Atropine produced limited cardiovascular effects and so a high dose was chosen as being one for which there is literature evidence of profound muscarinic receptor blockade. This dose-ranging study involved four rats in which cumulative doses of each of the 3 drugs were given on a dose-doubling basis. Doses of each of the drugs were given as i.v. bolus injections every 5 minutes with 1 hour between different drugs. The order of injections were: for animal 1—S, R, A; animal 2—R, A, S; animal 3—A, S, R and animal 4—R, A, S. As indicated above the doses and routes of injection where chosen as supernormal and above doses producing effects when given by inhalation.

From this study the following doses chosen for the subsequent interaction study:
R=8 µg/kg—8 µg/mL in 0.9% saline
S=2 µg/kg—2 µg/mL in 0.9% saline
A=32 µg/kg—32 µg/mL in 0.9% saline
(II) Interaction Study In this study all drugs were given as a single dose by i.v. bolus injection, via a jugular vein cannula, and at a volume of 1 mL/kg. The study design was blind and random with three lines each containing four animals for a total of 12 animals.

Pairs of drugs were given to individual animals on a randomized blind basis using a line by line design where each line contained four rats with injections as follows: R1S2, S1R2, R1A2 and A1R2 (in random order where 1 indicates the first drug given and 2 indicates the second drug given 5 minutes after the first drug). A total of 3 lines were studied thus a total of 12 rats were used and none of the animals had to be replaced. The study was stopped after 12 animals for the purposes of a provisional analysis to determine if further study was warranted and, if so, were more lines and/or dose adjustments required (an adaptive design).

The blood pressure was measured from a carotid artery using a transducer whose output was processed by AD Instruments PowerLab 26T. The heart rate was calculated on a beat to beat basis from the ECG and blood pressure traces. Analysis was by LabChart 6. Measurements were made using the functions in LabChart 6.

All drug effects were measured at the time of peak response to each injection of drug. The time to peak response with salbutamol was approximately 20 seconds for blood pressure and 60 seconds for heart rate. For RPL554 the corresponding times were 60-80 seconds for blood pressure and 2-4.5 minutes for heart rate. For atropine, it was 4 minutes for both blood pressure and heart rate.

Data were recorded as systolic, diastolic and calculated mean blood pressure in mmHg while heart rate was recorded as beats/min. The values recorded were processed to provide drug-induced changes in blood pressure and heart rate from two control values. One of these was prior to the first injection and the second prior to the second injection. The calculated changes were also normalized to these two control values and expressed as either a negative value for a fall from control values or as positive for an increase from control values.
Results
Primary Pharmacodynamics

TABLE 3

Effects of RPL554, salbutamol and atropine, alone and after another drug, on changes from control (Δ) mean arterial blood pressure and mean heart rate in anaesthetized rats (n = 3 for each mean value)

| | ΔMBP (mmHg and %) | | ΔHR (bpm and %) | |
|---|---|---|---|---|
| Effect of RPL554 when paired with salbutamol or atropine | | | | |
| RPL554 before salbutamol* | −15 | −15% | 36 | 10% |
| RPL554 after salbutamol** | −17 | −16% | 29 | 7% |

TABLE 3-continued

Effects of RPL554, salbutamol and atropine, alone and after another drug, on changes from control (Δ) mean arterial blood pressure and mean heart rate in anaesthetized rats (n = 3 for each mean value)

| | ΔMBP (mmHg and %) | | ΔHR (bpm and %) | |
|---|---|---|---|---|
| RPL554 before atropine* | −17 | −16% | 30 | 8% |
| RPL554 after atropine** | −19 | −20% | 33 | 10% |
| Effect of salbutamol when paired with RLP554 | | | | |
| Salbutamol before RPL554* | −32 | −30% | 58 | 18% |
| Salbutamol after RPL554*** | −23 | −24% | 43 | 11% |
| Effect of atropine when paired with RPL554 | | | | |
| Atropine before RPL554* | −5.0 | −5% | 6.3 | 1% |
| Atropine after RPL554**** | −2.7 | −3% | 21 | 5% |

Drugs were given as i.v. bolus injections in pairs 5 minutes apart. Δ values are the difference in peak effects from the pre-drug value, expressed as change or percentage change with respect to pre-drug values
* = control response to drug with no prior drug treatment The primary pharmacodynamic variables measured were systolic and diastolic blood pressure with computed mean blood pressure, and heart rate. The summary of the changes seen are shown in Table 3 above.

As can be seen in all cases, at the dose studied, RPL554 produced a fall in blood pressure, regardless of whether systolic, diastolic or mean pressures were expressed as actual changes, or normalized for pre-drug values. When measured before or after the prior administration of salbutamol or atropine, changes in blood pressure to RPL554 injection were not different, as can be seen in Table 3, whether changes were expressed as changes from pre-drug, or were normalized as a percentage.

Heart rate responses were similarly not influenced by the prior administration of the other drugs although the administration of the second drug 5 minutes after the first did change pre-drug values in a manner that depended on the drug considered.
Secondary Pharmacodynamics and Safety Pharmacology The secondary pharmacodynamic variables were: ECG, respiratory rate and arrhythmias. No significant changes were seen in the ECG or respiratory rate, and no arrhythmias were seen.
Pharmacodynamic Drug Interactions Possible cardiovascular interactions between the three drugs were the primary aim of the study. No major interactions between the drugs were seen as presented in Table 3 or seen by inspection of the actual experimental records.

Example 2

In Vivo Synergistic Effect of RPL554 Administered in Combination with Atropine (a Muscarinic Receptor Antagonist)

This Example investigates the ability of RPL554 to reverse the bronchoconstriction induced by bombesin and potential synergistic effects when RPL554 is administered in combination with atropine.

Guinea pigs were anaesthetised and ventilated. Airway obstruction was induced by the intravenous administration of bombesin (2 µg/ml; 5 ml/hr). Bronchodilation was induced by the iv. administration of RPL554 alone at various doses, or in combination with sub maximal doses of atropine (2 µg/kg). Doses selected following studies generating a dose-response curve for atropine to select a dose resulting in approximately 20% reduction in airways obstruction. Total lung resistance ($R_L$) and mean arterial blood pressure were measured. Data are expressed as % reduction in airways obstruction or blood pressure.

RPL554 caused a dose-dependent relaxation of guinea pig airways from 10-80 μg/kg. In combination with 2 μg/kg atropine (a dose that caused 22.3+4.9% reduction in airways obstruction), a submaximal dose of RPL554 (20 μg/kg) caused a greater relaxation of the airways than this dose of RPL554 administered alone (Table 4). The iv. administration (which was not potential when co-administered with either) of 20 μg/kg RPL554 caused a reduction in mean arterial blood pressure (control: 37.3+6.7%, +2 μg/kg atropine: 35.3+4.3%). The results are shown in FIGS. 7 to 10.

TABLE 4

| | % Reduction in airways obstruction | |
|---|---|---|
| | RPL554 control | RPL554 + atropine (2 μg/kg) |
| 10 μg/kg | 7.4 + 1.9 | 41.7 + 1.2 |
| 20 μg/kg | 24.6 + 4.3 | 76.5 + 8.8 |
| 40 μg/kg | 55.2 + 6.2 | 84.3 + 9.1 |
| 80 μg/kg | 65.1 + 5.3 | 81.9 + 4.7 |

The results provide further evidence that RPL554 is an effective bronchodilator which, when combined with the muscarinic receptor antagonist atropine, has synergistic activities as a bronchodilator, but does not interact with the drug classes on blood pressure.

Example 3

Synergistic Effect of RPL554 Administered in Combination with Glycopyrronium Bromide (a Muscarinic Receptor Antagonist) on Human Isolated Bronchi The long-lasting interaction between RPL554 and glycopyrronium in human isolated bronchi was investigated.
Methods Bronchial rings from 6 patients were incubated in Krebs-Henseleit solution (37° C.) aerated with $O_2/CO_2$ (95/5%) under 0.5-1.0 g tension. The duration of action (30% maximal relaxation, $EC_{30}$) of RPL554 and glycopyrronium, alone or in combination, was studied in tissue contracted with 3, 10 or 25 Hz electrical field stimulation (EFS). Bronchial tone was expressed as % of maximal response to papaverine ($E_{max}$) and the area under the curve (AUC) of the contractile response was assessed. Drug mixture effects were analyzed by Bliss Independence theory. Values (n=3) are mean±SEM.
Results RPL554 and glycopyrronium administered alone induced the maximal relaxation at 160±20 min and 50±10 min, respectively, and the effect was detectable for 4 hour. The maximal synergistic relaxant interaction was at ≅2 hrs (71.4±5.1%), during the washout period, and the combination of drugs extended the relaxant effect at 6 hrs, when the reduction of EFS-mediated contractile response was still 41.2±8.5%. The observed AUC (44.9±3.1%) was significantly lower than that expected (65.8±3.3%) during the 6 hrs of the study (P<0.001), with the main effectiveness for EFS at 3 Hz (−35.8±2.5%, P<0.001). The results are shown in FIGS. 11 to 16.
Conclusions RPL554 and glycopyrronium at low concentrations synergistically inhibited the contractile tone induced by EFS in human isolated bronchi and extended the relaxant effect for 6 hrs.

Example 4

Figure 17:
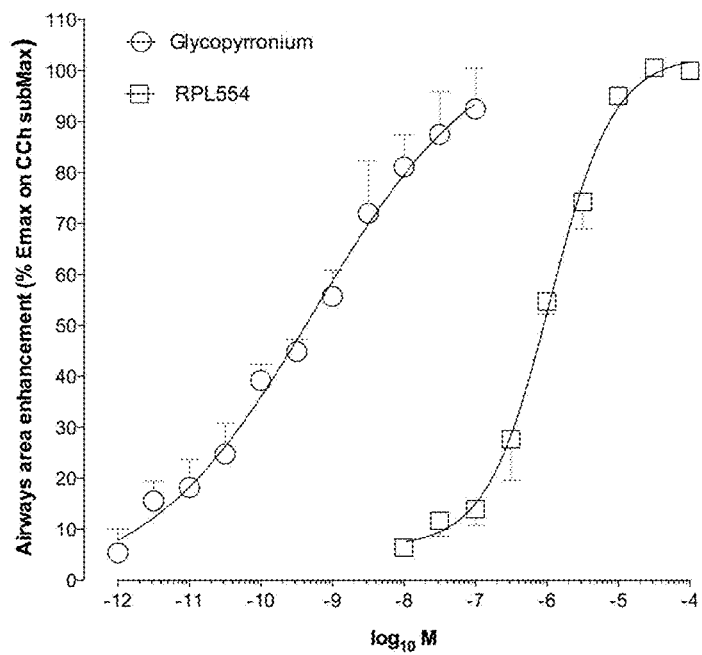
FIG. 17: Concentration response curves to RPL554 and glycopyrronium for human isolated bronchiles at sub-maximal contraction induced carbachol (CCh).
Figure 18:
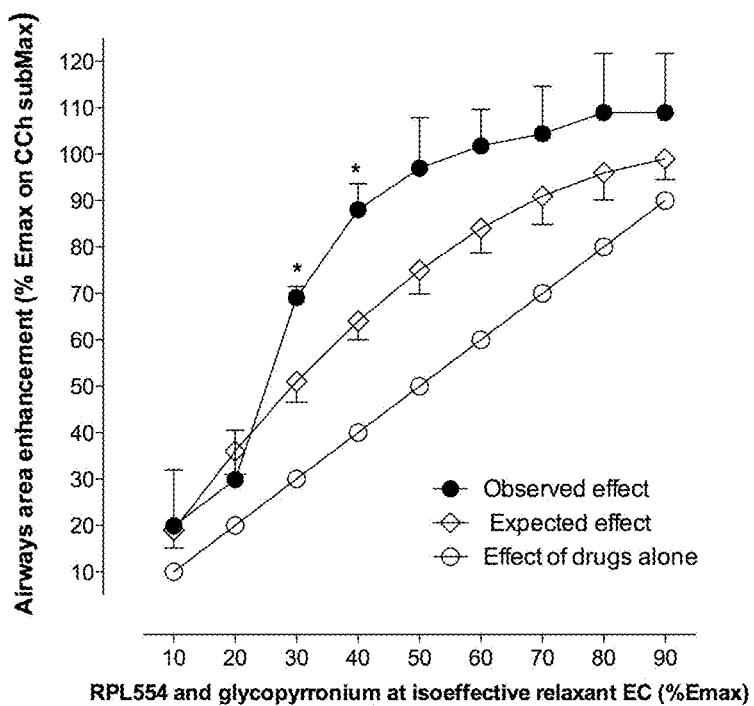
FIG. 18: Expected and observed relaxant response induced by RPL554 and glycopyrronium in combination for small human bronchi (<1 mm diameter).
Figure 19:
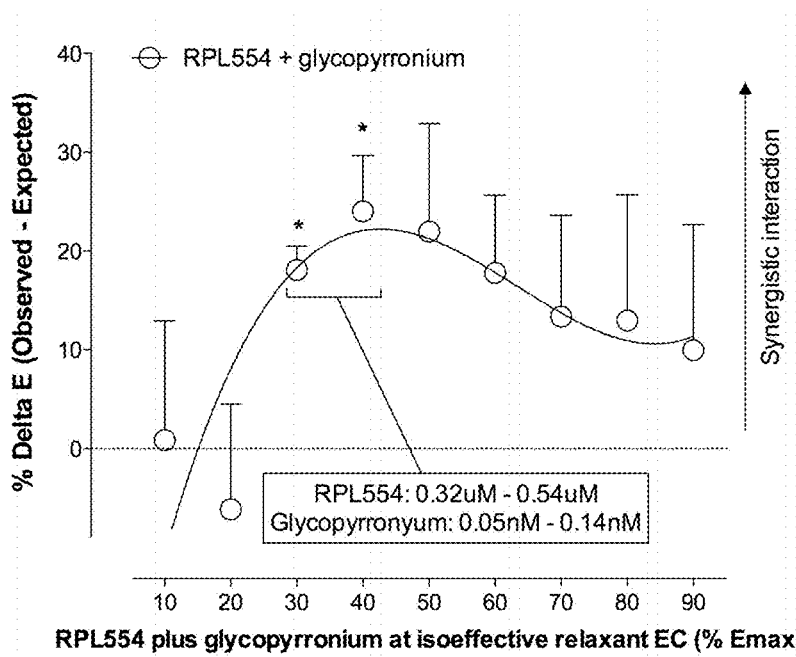
FIG. 19: Delta effect between observed and expected relaxant response induced by RPL554 and glycopyrronium in combination.

Synergistic Effect of RPL554 Administered in Combination with Glycopyrronium Bromide (a Muscarinic Receptor Antagonist) on Small Human Airways The interaction between RPL554 and glycopyrronium in human isolated bronchiles was investigated.
Methods Precision cut lung slices (PCLSs) from 6 patients were incubated in Krebs-Henseleit solution (37° C.) aerated with $O_2/CO_2$ (95:5%). The concentration response to RPL554 and glycopyrronium, administered alone and in combination at isoeffective concentrations, was assessed at sub-maximal contraction (70% maximum, $EC_{70}$) induced by carbachol (CCh). The relaxation of small bronchi (<1 mm diameter) was expressed as % of maximal response (lumen area enhancement) induced by papaverine ($E_{max}$) and potency as the negative logarithm of $IC_{50}$ ($pD_2$). Drug mixture effects were analyzed by Bliss Independence theory. Values (n=3) are mean±SEM.
Results Glycopyrronium induced a more potent concentration-dependent relaxation of bronchioles compared with RPL554 ($pD_2$: glycopyrronium 9.2±0.4, RPL554 6.0±0.1, P<0.001) and both abolished the CCh-induced contraction. Glycopyrronium and RPL554 at low-to-middle concentrations (glycopyrronium 0.05 nM-0.14 nM, RPL554 0.32 μM-0.54 μM) had a synergistic relaxant response on small airway enhancing relaxation by +21.1±4.0%, compared with the expected response (P<0.05). Low concentrations ($EC_{30}$) of glycopyrronium plus RPL554 induced significant (P<0.05) lumen area enhancement of 69.1±2.4%, compared with the expected response (51.0±5.4%). The results are shown in FIGS. 17 to 19.
Conclusions RPL554 and glycopyrronium had a synergistic interaction on the lumen area enhancement of bronchioles, mainly at low-to-middle concentrations.

Example 5

Synergistic Effect of RPL554 Administered in Combination with Tiotropium Bromide (a Muscarinic Receptor Antagonist)

The method of Example 1 for evaluating the synergistic effect of the combination of RPL554 and atropine is repeated for the muscarinic receptor antagonist tiotropium bromide. Concentration response curves are constructed to test RPL554 alone, tiotropium bromide alone, and RPL554 administered in combination with tiotropium bromide. The Berenbaum Method and the Bliss Independence criteria are used to evaluate synergistic action between tiotropium bromide and RPL554. A synergistic effect is observed for the combination of RPL554 and tiotropium bromide.

Example 6

Synergistic Effect of RPL554 Administered in Combination with Oxitropium Bromide (a Muscarinic Receptor Antagonist)

The method of Example 1 for evaluating the synergistic effect of the combination of RPL554 and atropine is repeated for the muscarinic receptor antagonist oxitropium bromide. Concentration response curves are constructed to test RPL554 alone, oxitropium bromide alone, and RPL554 administered in combination with oxitropium bromide. The Berenbaum Method and the Bliss Independence criteria are used to evaluate synergistic action between oxitropium bromide and RPL554. A synergistic effect is observed for the combination of RPL554 and oxitropium bromide.

Example 7

Synergistic Effect of RPL554 Administered in Combination with Aclidinium (a Muscarinic Receptor Antagonist)

The method of Example 1 for evaluating the synergistic effect of the combination of RPL554 and atropine is repeated for the muscarinic receptor antagonist aclidinium. Concentration response curves are constructed to test RPL554 alone, aclidinium alone, and RPL554 administered in combination with aclidinium. The Berenbaum Method and the Bliss Independence criteria are used to evaluate synergistic action between aclidinium and RPL554. A synergistic effect is observed for the combination of RPL554 and aclidinium.

Formulation Example 1—Administration by a DPI

RPL554 combination (0.2 mg) is micronized and then blended with lactose (25 mg). This blended mixture is then loaded into a gelatin inhalation cartridge. The contents of the cartridge are administered using a DPI, for example.

A micronized RPL554 combination (100 mg) is blended with milled lactose (25 g) (e.g., lactose in which not greater than about 85% of the particles have a MMD of about 60 μm to about 90 μm and not less than 15% of the particles have a MMD of less then 15 μm). The blended mixture is then loaded into individual blisters of a peelable blister pack in an amount sufficient to provide about 10-500 μg of the RPL554 per dose. The contents of the blisters are administered using a DPI.

Alternately, a micronized RPL554 combination (1 g) is blended with milled lactose (200 g) to form a bulk composition having a weight ratio of compound to milled lactose of 1:200. The blended composition is packed into a DPI capable of delivering between about 10-500 μg of the RPL554 per dose.

Alternately, a micronized RPL554 (100 mg) and a micronized muscarinic receptor antagonist (500 mg) are blended with milled lactose (30 g). The blended mixture is then loaded into individual blisters of a peelable blister pack in an amount sufficient to provide about 10 μg to about 500 μg of the RPL554 per dose. The contents of the blisters are administered using a DPI.

Formulation Example 2—Compositions for Use in an MDI

A micronized RPL554 combination (10 g) is dispersed in a solution prepared by dissolving lecithin (0.2 g) in demineralized water (200 mL). The resulting suspension is spray dried and then micronized to form a micronized composition comprising particles having a mean diameter less than about 1.5 The micronized composition is then loaded into MDI cartridges containing pressurized 1,1,1,2-tetrafluoroethane in an amount sufficient to provide about 10 μg to about 500 μg of the RPL554 per dose when administered by the MDI.

Alternately, a suspension containing 5 wt % RPL554 combination, 0.5 wt % lecithin, and 0.5 wt % trehalose is prepared by dispersing 5 g of a RPL554 combination as micronized particles with mean size less than 10 μm in a colloidal solution formed from 0.5 g of trehalose and 0.5 g of lecithin dissolved in 100 mL of demineralized water. The suspension is spray dried and the resulting material is micronized to particles having a mean diameter less than 1.5 The particles are loaded into canisters with pressurized 1,1,1,2-tetrafluoroethane.

Formulation Example 3—Composition for Use in a Nebulizer Inhaler

RPL554 combination (25 mg) is dissolved in citrate buffered (pH 5) isotonic saline (125 mL). The mixture is stirred and sonicated until the compound is dissolved. The pH of the solution is checked and adjusted, if necessary, to pH 5 by slowly adding aqueous 1N sodium hydroxide. The solution is administered using a nebulizer device that provides about 10 μg to about 500 μg of the RPL554 combination per dose.

Formulation Example 4—Hard Gelatin Capsules for Oral Administration

RPL554 combination (50 g), spray-dried lactose (440 g) and magnesium stearate (10 g) are thoroughly blended. The resulting composition is then loaded into hard gelatin capsules (500 mg of composition per capsule).

Formulation Example 5—Suspension for Oral Administration

The following ingredients are mixed to form a suspension containing 100 mg of compound per 10 mL of suspension:

| Ingredients | Amount |
| --- | --- |
| RPL554 combination | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum$^{RTM}$ K (magnesium aluminum silicate) | 1.0 g |
| Flavoring | 0.035 mL |
| Colorings | 0.5 mg |
| Distilled water q.s. | to 100 mL |

Formulation Example 5—Injectable Formulation for Administration by Injection

RPL554 combination (0.2 g) is blended with 0.4 M sodium acetate buffer solution (2.0 mL). The pH of the resulting solution is adjusted to pH 4 using 0.5 N aqueous hydrochloric acid or 0.5 N aqueous sodium hydroxide, as necessary, and then sufficient water for injection is added to provide a total volume of 20 mL. The mixture is then filtered through a sterile filter (0.22 micron) to provide a sterile solution suitable for administration by injection.

REFERENCES

Berenbaum M C (1977) Synergy, additivism and antagonism in immunosuppression. A critical review. Clin Exp Immunol 28:1-18.

Binks A P, Paydarfar D, Schachter S C, Guz A and Banzett R B (2001) High strength stimulation of the vagus nerve in awake humans: a lack of cardiorespiratory effects. Respir Physiol 127:125-133.

Boik J C, Newman R A and Boik R J (2008) Quantifying synergism/antagonism using nonlinear mixed-effects modeling: a simulation study. Stat Med 27:1040-1061.

Boswell-Smith V, Cazzola M and Page C P (2006a) Are phosphodiesterase 4 inhibitors just more theophylline? J Allergy Clin Immunol 117:1237-1243.

Boswell-Smith V, Spina D, Oxford A W, corner M B, Seeds E A and Page C P (2006b) The pharmacology of two novel long-acting phosphodiesterase 3/4 inhibitors, RPL554 [9,10-dimethoxy-2(2,4,6-trimethylphenylimino)-3-(n-carbamoyl-2-aminoethyl)-3,4,6,7-tetrahydro-2H-pyrimido[6,1-a]isoquinolin-4-one] and RPL565 [6,7-dihydro-2-(2,6-diisopropylphenoxy)-9,10-dimethoxy-4H-pyrimido[6,1-a]isoquinolin-4-one]. J Pharmacol Exp Ther 318:840-848.

Boucher A N and Tam V H (2006) Mathematical formulation of additivity for antimicrobial agents. Diagn Microbiol Infect Dis 55:319-325.

Freas W, Hart J L, Golightly D, McClure H and Muldoon S M (1989) Contractile properties of isolated vascular smooth muscle after photoradiation. Am J Physiol 256:H655-664.

Goldoni M and Johansson C (2007) A mathematical approach to study combined effects of toxicants in vitro: evaluation of the Bliss independence criterion and the Loewe additivity model. Toxicol In Vitro 21:759-769.

Goodman L S, Gilman A and Brunton L L (2008) Goodman & Gilman's manual of pharmacology and therapeutics. McGraw-Hill Medical, New York.

Grabovsky Y and Tallarida R J (2004) Isobolographic analysis for combinations of a full and partial agonist: curved isoboles. J Pharmacol Exp Ther 310:981-986.

Greco W R, Bravo G and Parsons J C (1995) The search for synergy: a critical review from a response surface perspective. Pharmacol Rev 47:331-385.

Hatake K and Wakabayashi I (2000) Ethanol suppresses L-arginine-induced relaxation response of rat aorta stimulated with bacterial lipopolysaccharide. Nihon Arukoru Yakubutsu Igakkai Zasshi 35:61-68.

Meletiadis J, Mouton J W, Meis J F and Verweij P E (2003) In vitro drug interaction modeling of combinations of azoles with terbinafine against clinical Scedosporium prolificans isolates. Antimicrob Agents Chemother 47:106-117.

Mercier F J, Naline E, Bardou M, Georges O, Denjean A, Benhamou D and Advenier C (2002) Relaxation of proximal and distal isolated human bronchi by halothane, isoflurane and desflurane. Eur Respir J 20:286-292.

Motulsky H (1995) Intuitive biostatistics. Oxford University Press, New York; Oxford.

Motulsky H and Christopoulos A (2004) Fitting models to biological data using linear and nonlinear regression: a practical guide to curve fitting. Oxford University Press, Oxford.

Rabe K F (1998) Mechanisms of immune sensitization of human bronchus. Am J Respir Crit Care Med 158:S161-170.

Spina D, Ferlenga P, Biasini I, Moriggi E, Marchini F, Semeraro C and Page C P (1998) The effect duration of selective phosphodiesterase inhibitors in the guinea pig. Life Sci 62:953-965.

Tallarida R J (2001) Drug synergism: its detection and applications. J Pharmacol Exp Ther 298:865-872.

Tallarida R J (2006) An overview of drug combination analysis with isobolograms. J Pharmacol Exp Ther 319:1-7.

Tallarida R J and Raffa R B (2010) The application of drug dose equivalence in the quantitative analysis of receptor occupation and drug combinations. Pharmacol Ther 127:165-174.

Watson N, Bodtke K, Coleman R A, Dent G, Morton B E, Ruhlmann E, Magnussen H and Rabe K F (1997) Role of IgE in hyperresponsiveness induced by passive sensitization of human airways. Am J Respir Crit Care Med 155:839-844.

The invention claimed is:

1. A nebulizer inhaler, a dry powder inhaler or a metered dose inhaler comprising:
   (i) a composition which comprises (a) a therapeutically effective amount of a PDE3/PDE4 inhibitor which is 9,10-Dimethoxy-2-(2,4,6-trimethylphenylimino)-3-(N-carbamoyl-2-aminoethyl)-3,4,6,7-tetrahydro-2H-pyrimido[6,1-a]isoquinolin-4-one or a pharmaceutically acceptable acid addition salt thereof, and (b) a therapeutically effective amount of a muscarinic receptor antagonist which is selected from the group consisting of atropine, methylatropine, homatropine, hyoscyamine, hyoscine, glycopyrrolate, ipratropium, oxitropium, clidinium and mepenzolate; and
   (ii) one or more pharmaceutically acceptable carriers, diluents, or excipients.

2. A nebulizer inhaler, a dry powder inhaler or a metered dose inhaler composition according to claim 1, in which the PDE3/PDE4 inhibitor (a) is 9,10-Dimethoxy-2-(2,4,6-trimethylphenylimino)-3-(N-carbamoyl-2-aminoethyl)-3,4,6,7-tetrahydro-2H-pyrimido[6,1-a]isoquinolin-4-one.

3. A nebulizer inhaler, a dry powder inhaler or a metered dose inhaler composition according to claim 1 or 2, in which the muscarinic receptor antagonist (b) is atropine, hyoscine, glycopyrrolate, ipratropium or oxitropium.

4. A nebulizer inhaler, a dry powder inhaler or a metered dose inhaler composition according to claim 1, in which the muscarinic receptor antagonist (b) is atropine or glycopyrrolate.

5. A nebulizer inhaler, a dry powder inhaler or a metered dose inhaler composition according to claim 1, wherein the composition is a fixed combination.

6. A method of treating a disease or condition which is based on acute or chronic obstruction of bronchi or vessels in the respiratory tract, in a subject in need thereof, which method comprises administering by inhalation to said subject (a) a therapeutically effective amount of a PDE3/PDE4 inhibitor which is 9,10-Dimethoxy-2-(2,4,6-trimethylphenylimino)-3-(N-carbamoyl-2-aminoethyl)-3,4,6,7-tetrahydro-2H-pyrimido[6,1-a]isoquinolin-4-one or a pharmaceutically acceptable acid addition salt thereof, and (b) a therapeutically effective amount of a muscarinic receptor antagonist which is selected from the group consisting of atropine, methylatropine, homatropine, hyoscyamine, hyoscine, glycopyrrolate, ipratropium, oxitropium, clidinium and mepenzolate.

7. A method according to claim 6, wherein the muscarinic receptor antagonist is selected from the group consisting of atropine, hyoscine, and glycopyrrolate.

8. A method according to claim 6, wherein the disease or condition is asthma or chronic obstructive pulmonary disease (COPD).

9. A method according to claim 6, wherein said subject is a human.

10. A method of treating a disease or condition in a subject in need thereof, which method comprises administering by inhalation to said subject (a) a therapeutically effective amount of a PDE3/PDE4 inhibitor which is 9,10-Dimethoxy-2-(2,4,6-trimethylphenylimino)-3-(N-carbamoyl-2-aminoethyl)-3,4,6,7-tetrahydro-2H-pyrimido[6,1-a]isoquinolin-4-one or a pharmaceutically acceptable acid addition salt thereof simultaneously, separately or sequentially in combination with (b) a therapeutically effective amount of a muscarinic receptor antagonist which is selected from the group consisting of atropine, methylatropine, homatropine, hyoscyamine, hyoscine, glycopyrrolate, ipratropium, oxitropium, clidinium and mepenzolate,
  wherein the disease or condition is selected from the group consisting of asthma, allergic asthma, bronchitis, emphysema, bronchiectasis, chronic obstructive pulmonary disease (COPD), adult respiratory distress syndrome (ARDS), steroid resistant asthma, severe asthma and pediatric asthma.

* * * * *